(12) United States Patent
Cates

(10) Patent No.: US 12,052,333 B2
(45) Date of Patent: Jul. 30, 2024

(54) CONTINUOUS TIME ADJUSTMENT DAYLIGHT SAVING TIME METHOD AND APPARATUS

(71) Applicant: Rambler Wheels, LLC, Dripping Springs, TX (US)

(72) Inventor: John Cates, Dipping Springs, TX (US)

(73) Assignee: Rambler Wheels, LLC, Dripping Springs, TX (US)

( * ) Notice: Subject to any disclaimer, the term of this patent is extended or adjusted under 35 U.S.C. 154(b) by 0 days.

(21) Appl. No.: 17/774,780

(22) PCT Filed: Nov. 7, 2020

(86) PCT No.: PCT/US2020/059567
§ 371 (c)(1),
(2) Date: May 5, 2022

(87) PCT Pub. No.: WO2021/092512
PCT Pub. Date: May 14, 2021

(65) Prior Publication Data
US 2022/0377160 A1    Nov. 24, 2022

Related U.S. Application Data

(60) Provisional application No. 62/933,106, filed on Nov. 8, 2019.

(51) Int. Cl.
*H04L 12/00* (2006.01)
*G04B 19/00* (2006.01)
(Continued)

(52) U.S. Cl.
CPC .............. *H04L 69/28* (2013.01); *G04B 19/00* (2013.01); *G04C 19/00* (2013.01); *H04L 69/22* (2013.01)

(58) Field of Classification Search
None
See application file for complete search history.

(56) References Cited

U.S. PATENT DOCUMENTS 5,195,025 A *  3/1993  Boecker ................... G06F 1/14
                                                       700/16
2003/0193842 A1  10/2003  Harrison
(Continued)

OTHER PUBLICATIONS

Barnes et al., Changing to Daylight Saving Time Cuts into Sleep and Increases Workplace Injuries, Journal of Applied Psychology, 2009, vol. 94, No. 5, American Psychological Association, 13 pages.

*Primary Examiner* — Sai Aung
*Assistant Examiner* — Lionel Preval
(74) *Attorney, Agent, or Firm* — Patent Capital Group

(57) ABSTRACT

There is disclosed in one example a method of observing continuous daylight adjustment (CDA) time, including: commencing at a first transition date observing an annual spring-forward period including lengthened social seconds, wherein a lengthened social second is longer than a standard scientific second; commencing at a second transition date observing an annual fall-back period including shortened social seconds, wherein a shortened social second is shorter than a standard scientific second; and computing and electronically displaying in a human-readable format a current social time different from a current scientific time.

33 Claims, 12 Drawing Sheets

(51) Int. Cl.
  *G04C 19/00*  (2006.01)
  *H04L 69/22*  (2022.01)
  *H04L 69/28*  (2022.01)

(56) References Cited

U.S. PATENT DOCUMENTS

| | | | |
|---|---|---|---|
| 2004/0151072 A1* | 8/2004 | Yamamoto | G04G 9/0076 368/29 |
| 2004/0223515 A1* | 11/2004 | Rygielski | G04G 7/00 370/503 |
| 2006/0022761 A1 | 2/2006 | Abeles et al. | |
| 2006/0140056 A1* | 6/2006 | Lizzi | G04B 19/23 368/21 |
| 2007/0200643 A1 | 8/2007 | Dimarcq et al. | |
| 2007/0282159 A1 | 12/2007 | Sato et al. | |
| 2008/0293537 A1 | 11/2008 | Phillips | |
| 2010/0254229 A1 | 10/2010 | Kury et al. | |
| 2011/0151415 A1 | 6/2011 | Darling | |
| 2014/0250050 A1 | 9/2014 | Lospinoso et al. | |

* cited by examiner

US 12,052,333 B2

CONTINUOUS TIME ADJUSTMENT DAYLIGHT SAVING TIME METHOD AND APPARATUS

CROSS-REFERENCE TO RELATED APPLICATION

This Application claims priority to PCT/US2020/059567, filed Nov. 7, 2022, which also claims priority to U.S. Provisional Patent Application 62/933,106, filed Nov. 8, 2019 and entitled "Continuous Time Adjustment Daylight Saving Time Method and Apparatus", both applications are incorporated herein by reference in their entirety.

FIELD OF THE SPECIFICATION

This application relates in general to time management, and more particularly, though not exclusively, to a system and method for providing a continuous time adjustment Daylight Saving Time method and apparatus.

BACKGROUND

Daylight Saving Time (DST) is observed in many jurisdictions.

BRIEF DESCRIPTION OF THE DRAWINGS

The present disclosure is best understood from the following detailed description when read with the accompanying FIGURES. It is emphasized that, in accordance with the standard practice in the industry, various features are not necessarily drawn to scale, and are used for illustration purposes only. Where a scale is shown, explicitly or implicitly, it provides only one illustrative example. In other embodiments, the dimensions of the various features may be arbitrarily increased or reduced for clarity of discussion. Furthermore, the various block diagrams illustrated herein disclose only one illustrative arrangement of logical elements. Those elements may be rearranged in different configurations, and elements shown in one block may, in appropriate circumstances, be moved to a different block or configuration.

SUMMARY

Figure 1:
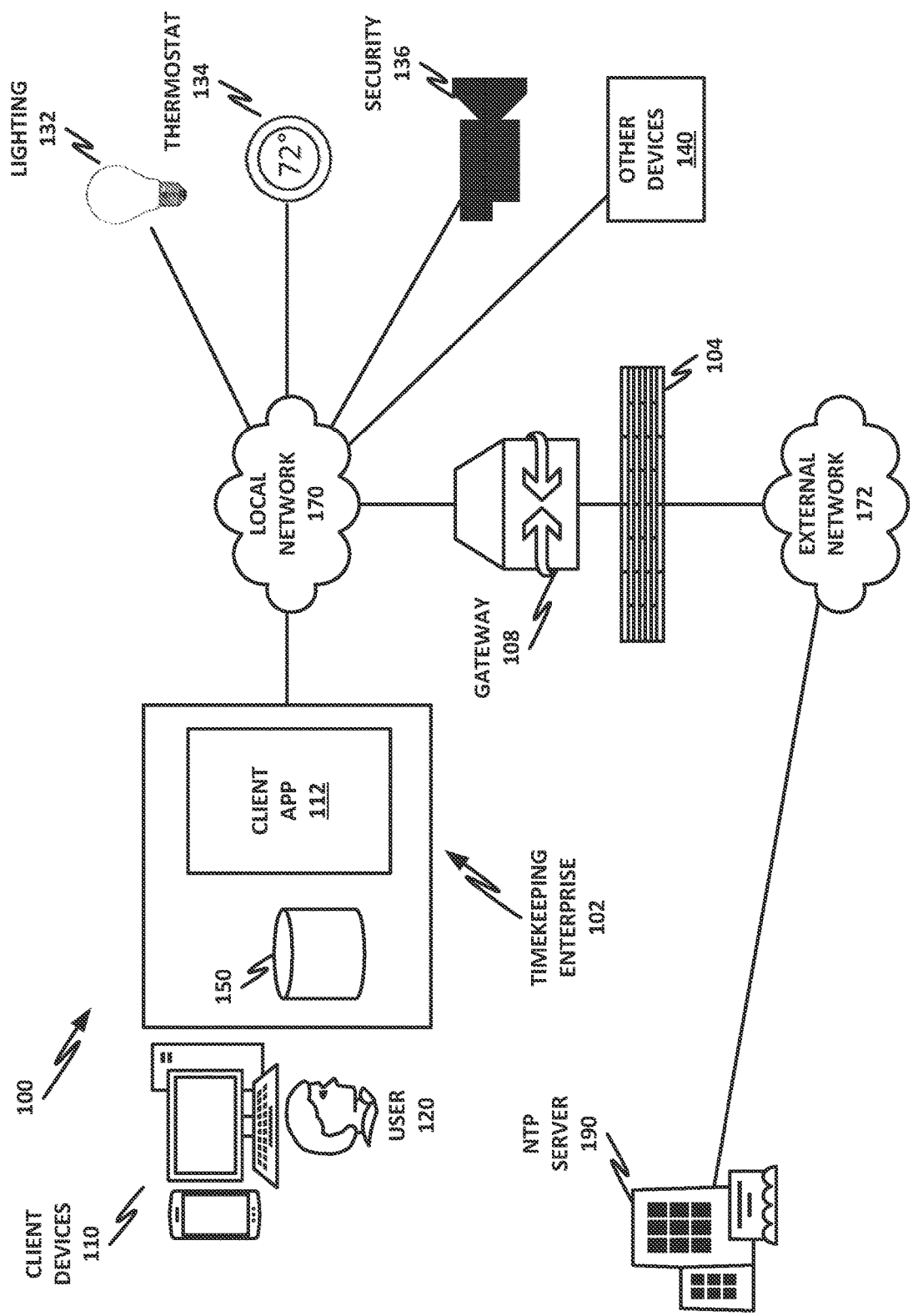
FIG. 1 is a block diagram of selected elements of an interconnected computing ecosystem.

In an example, there is disclosed a method of observing continuous daylight adjustment (CDA) time, comprising: commencing at a first transition date observing an annual spring-forward period comprising lengthened social seconds, wherein a lengthened social second is longer than a standard scientific second; commencing at a second transition date observing an annual fall-back period comprising shortened social seconds, wherein a shortened social second is shorter than a standard scientific second; and computing and electronically displaying in a human-readable format a current social time different from a current scientific time.

EMBODIMENTS OF THE DISCLOSURE

The following disclosure provides many different embodiments, or examples, for implementing different features of the present disclosure. Specific examples of components and arrangements are described below to simplify the present disclosure. These are, of course, merely examples and are not intended to be limiting. Further, the present disclosure may repeat reference numerals and/or letters in the various examples. This repetition is for the purpose of simplicity and clarity and does not in itself dictate a relationship between the various embodiments and/or configurations discussed. Different embodiments may have different advantages, and no particular advantage is necessarily required of any embodiment.

Daylight Saving Time (DST) is a phenomenon that is hundreds of years old, at least in concept, and that many people have a sort of love/hate relationship with. On the one hand, many people enjoy having daylight hours extend late during the summer, so that they can enjoy shopping and activities in the daylight, even late in the evening hours. In fact, this has led to some proposals in the past to observe a year-round DST, so that more daylight hours are observed in the evening. However, this can be problematic in the winter, because those daylight hours are taken from the morning. This means that young children attending school may be waiting for a bus in the dark, or that people who go to work early are driving to work in the dark. Thus, within the United States and in many other jurisdictions throughout the world, the time changes of DST continue to be observed to provide later daylight hours in the spring and summer, and earlier daylight hours in the fall and winter.

However, these time changes come at a cost. Many individuals and families are frustrated by the abrupt change in time that occurs twice a year. This disrupts sleep schedules, and can be particularly problematic for younger children who have a hard time adjusting to the schedule that changes suddenly twice a year. Indeed, some studies have linked DST observance with an increase in industrial accidents, a decrease in work productivity, and other negative effects.

It is therefore beneficial to provide a method that jurisdictions could adopt to gain the benefits of DST, without the abrupt time changes necessitated by the current protocol. Advantageously, the inventor of the technology disclosed in the present specification has observed that the benefits of DST can be realized with minimal disruption to the routines of users. This can be achieved, in some cases, by one of two methods.

In one embodiment, a number of "leap seconds" can be added or removed at the end of each day, to provide a continuous time adjustment that tracks substantially with the benefits of DST, but provides a gradual adjustment that is spread out over the space of several months. The use of leap seconds may be advantageous, because this enables the observation of true seconds that track with the international standard for a second. A standard international (SI) second is defined as the time that elapses during 9,192,631,000,770 (9.192631770×10⁹) cycles of the radiation produced by the transition between two levels of the cesium 133 atom. There have also been proposals to define a second in terms of electromagnetic field propagation, namely to define a second as the time required for an electromagnetic field (such as light) to propagate 299,792,458 meters through a vacuum. These rigid definitions of a second provide consistency for scientists and enable highly precise measurements in scientific instruments. Throughout this specification, a second conforming to the SI definition of one second will be referred to as a "scientific second."

In this proposed embodiment, a number of scientific seconds (on the order of approximately 20 scientific seconds) may be added to or removed from each day at a reasonable time. For example, the current observation of DST inserts or removes one hour at approximately 2:00 AM on two specified dates each year. In one embodiment, approximately 20 leap seconds may be added or subtracted at the same time (i.e., approximately 2:00 AM). The exact number of leap seconds inserted or removed would depend on the specific embodiment. For example, in current practice in the United States, DST lasts for approximately eight months of the year, while standard time lasts for only approximately four months of the year.

If the same timing were observed, then to gradually "fall back" one hour over a span of eight months (i.e., approximately 244 days), then between 14 and 15 seconds would be subtracted from each day, so that at a "crossover point," the time has been adjusted to "fall back" one hour. On the other hand, over the course of four months (approximately 122 days), between 29 and 30 seconds would need to be added each day to gradually "spring forward" over that period of four months. The result of these adjustments is that societies gain the benefit of having later daylight hours in the summer and earlier daylight hours in the winter, but without the jarring, immediate change of a full hour twice a year. It would be relatively easy for users to gradually adjust to a time change of 15 to 30 seconds a day, every day, instead of a full hour twice a year. Note that the division between eight months and four months is provided here by way of illustration only. Any other schedule could be used, such as dividing between six months and six months. In that case, each period would be approximately 183 days, and between 19 and 20 leap seconds would be added to or subtracted from each day to realize the continuous time adjustment DST.

As long as these time changes are scheduled in advance and well understood, it is within the skill of a person having ordinary skill in the art of computer programming to program a time system to add or subtract these extra leap seconds on a given schedule.

While this system is relatively straightforward for a digital computer, and has the advantage of maintaining correlation with the scientific second, it would be more difficult to implement for analog watches that rely on mechanical gears and gearing ratios. In another embodiment, instead of adding or subtracting leap seconds for each day, a "social second" may be defined. The social second is of variable time, and differs from the scientific second discussed earlier in this specification. Again, the length of a social second would depend on the span used for DST. For example, DST traditionally begins on a Sunday morning in early March and ends on a Sunday morning in early November. This causes DST transitions to fall on a weekend, to give users a day or so to adjust to the new time. Because the present solution provides continuous adjustment, it does not require a weekend transition, so any arbitrary date may be selected.

For example, daylight saving could begin on March 1 and end on November 1. The eight-month period of DST would be approximately 35 weeks, or approximately 21,168,000 seconds. The standard time of four months would be approximately 17 weeks and one day, or in a leap year, 17 weeks and two days. This is approximately 10,368,000 seconds. The "fall back" for November 1 could be spread throughout the eight months, and built into every social second. In other words, the social second for this time would be slightly shorter than a scientific second. Instead of equaling one scientific second, a social second would equal on the order of 0.9982993 seconds during the fall back time.

Inversely, during the four months of the year for standard time, the "spring forward" hour could be added to every second during that time. Thus, instead of being equal to one scientific second, a social second would equal on the order of 1.00034722 scientific seconds. Advantageously, even a mechanical watch with gears could be provided with different-sized gears to provide the appropriate ratios. Precise machining techniques available in modern practice would enable the manufacture of two gears, so that one gear engages the minute gear during the fall back time, and a different gear engages the minute gear during spring forward time. Instead of being precisely 1/60th of the minute gear, these new gears would be sized to provide a social second of 0.9982993 and 1.00034722 social seconds, respectively. A manual switch or button, or an automated gear, could be used to switch between the two gears.

Alternatively, the gears of the above embodiment may be cast, forged, or otherwise manufactured according to the teachings of the present specification.

Note that the foregoing embodiments anticipate adding or subtracting defined social seconds around the current eight-month and four-month rotations for DST. This is provided by way of illustration only. Other ratios could be used, particularly a six-month to six-month ratio, or the approximately seven-month to five-month ratio that was used in the United States prior to 2007.

Furthermore, the spring forward and fall back switchover times need not fall in March/April or October/November, as they have in the past. Rather, in some embodiments, to spread the time out more evenly, the switchover could happen at or around the winter solstice (approximately December 21st or 22nd) and the summer solstice (at or around June 20th). In other embodiments, any other switchover time could be used.

In various embodiments, time servers could also be provisioned to observe the new DST protocol, using either leap seconds or social seconds, and could provide signals to synchronize user equipment or endpoint devices with the correct time. Thus, even if an endpoint device uses the old time protocol, time servers observing the Network Time Protocol (NTP) could be used to correctly synchronize these devices. This would be advantageous in the interim, so that devices could be synchronized even when they have not switched over to the new protocol.

The foregoing proposals may result in a "social time" that varies from the International Atomic Time (TAI) by up to approximately one hour. However, this may also provide advantages. In the past, leap seconds have been inserted into the official National Institute of Standards and Technology (NIST) time to account for various physical irregularities, such as variations in the earth's orbital period. In the current proposal, it is recognized that social time will vary from the TAI time, and that there is no need to attempt to synchronize them with leap seconds. This elimination of leap seconds within TAI time is beneficial, because leap seconds can provide irregularities in scientific instruments.

Some challenges are evident in transitioning older devices to the newer time protocol. In the case of network-connected computing devices with a network time protocol (NTP) client, the difficulty can be minimized. In those cases, the device can simply be pointed at an NTP server that serves up the current social time. Alternatively, if the device is a scientific instrument that needs to keep the correct scientific time, it can operate as before, and/or be pointed at an NTP server that serves the currently correct scientific time.

Other challenges are presented by the difference between scientific time and social time. For example, even in jurisdictions that adopt a social time with continuous daylight adjustment features as described herein, many functions may continue to operate on the standard scientific second. For example, the standard scientific second as defined above may still be used for things like stopwatches, scientific measurements, sports records, and many other uses. Indeed, in some cases, the social time-based on the modified social second—may be used only for situations where a person might ask, "What time is it?"

Computing systems may be provisioned with dual time-keeping capabilities. A system may include a scientific time circuit, which provides the current scientific time, and may be used for purposes such as timestamps on files, measurements, and other purposes. A separate social time circuit may keep track of the current social time, and may be used to convert scientific time to social time for display purposes (e.g., when displaying the time to a user).

In an embodiment, a new protocol may be defined wherein an NTP query includes a flag, marker, header, or similar to indicate whether a request is for social time or scientific time. On the other hand, an NTP response may include a flag, marker, and/or header that indicates whether the time being served is the scientific or social time. Beneficially, a reserved field could be used for this flag or marker, so that legacy devices are still able to process responses from NTP servers that are configured to serve both social and scientific time. In some cases, separate servers could be set up to serve the different times (e.g., social.ntp.org and scientific.ntp.org to serve social and scientific time, respectively). In cases where it would be difficult for devices, such as internet of things (IoT) devices, to be configured to use new protocols or time servers, a home or enterprise gateway could be configured to include an NTP server, and the NTP server may be configured to serve social or scientific time to various devices, as desired for the deployment.

Difficulties may also be encountered in the case of analog clocks or watches, or older digital clocks that use the standard scientific time. Some of these devices are also configured to synchronize with NTP servers, and in the case of those devices, they can simply be served with the social time for display to a user. In the case of analog devices or older digital devices without such a capability, they may need to be adjusted periodically to keep up with the current social time. However, these devices have a finite lifespan, and may eventually be replaced with more modern devices that have social time capabilities. Another challenge may arise in the case of large and famous clocks that may be difficult to modify. For example, Big Ben is a famous clock in London, England that is configured to work on scientific time. While it is possible that some of the gears in Big Ben could be changed out with a pair of gears that keep time according to the social time, it may also be more desirable to simply allow Big Ben to continue keeping scientific time, with the understanding that if England were to adopt continuous daylight adjustment, the time as displayed would not match with the social time.

In the case of new analog watches that are intended to keep track of social time, a pair of gears may be provided, with each gear moving in a rotation according to the social time instead of the scientific time. Gearing ratios between the second and minute hands and the minute and hour hands can be maintained. In other words, even under the social time regimen, a social hour is still equal to 60 social minutes, and a social minute is still equal to 60 social seconds. Switching means such as a switch or lever may be provided to switch between the two gears, wherein one gear is used for the spring forward, and one gear is used for the fall back.

Another potential difficulty arises in the case of leap years. In leap years, there is an extra day that may occur, for example, within the fall back. In that case, the length of a social time may be adjusted during leap years to account for the extra day. Alternatively, normal social seconds may be observed even in leap years, and computer devices and NTP servers may be configured and programmed to simply account for the time lost or gained when switching over between the fall back span in the spring forward span.

Computers programmed to track social time may do so, in some embodiments, based on scientific time. As discussed above, endpoint devices with NTP capabilities need not be specifically programmed with social time circuits or modules. Instead, these devices may be configured to simply query an NTP server at regular intervals, such as once or twice a day, and adjust their time accordingly. While the devices will be out of sync with social time between queries, if the queries are frequent enough, the difference will be on the order of seconds or tens of seconds, which is generally considered within an acceptable margin of error for social functions. Indeed, legacy devices that do not have NTP capabilities are rarely more precise than this, anyway.

Advantageously, it is well within the ability of a modern computing device to keep track of and compute the difference between social time and scientific time. For example, calendar applications and scheduling modules are already programmed with the ability to convert between different time zones. In this case, a database may be maintained of jurisdictions that observe continuous daylight adjustment, versus those that observe standard time or traditional daylight saving time. For simplicity, newer devices configured to work with CDA time may be configured to store the system clock as Greenwich Mean Time (GMT), which may be maintained according to the standard scientific time. For display purposes, the system may then convert between GMT and CDA time for the current time zone. For example, many computers store scientific time as a number of seconds elapsed since a predefined epoch moment, such as Jan. 1, 1970. If the system clock stores time in GMT, then it may simply add or remove a number of hours or half-hours to account for the geographic time zone of the user. To convert to social time, the system may compute the number of seconds elapsed since the last CDA transition, and then multiply that value by the lengthened or shortened value of a second for the current CDA span, to arrive at the current CDA social time.

One interesting result of this is that meetings may start at odd times for users in jurisdictions that do not observe CDA. For example, a user using a scheduling or calendar application within a jurisdiction that observes CDA time may schedule a meeting for 10:00 AM. If the user schedules this with another user who lives in a jurisdiction that does not observe CDA time, then the meeting may occur at, for example, 10:07 AM for the non-CDA user. While this is an unusual meeting time for the non-CDA user, it may be understood that this difference is an artifact of the CDA protocol, and users will adjust to it. Ultimately, if a large majority of jurisdictions or all jurisdictions worldwide begin to observe CDA time, then these unusual artifacts will eventually disappear. Conversely, if the meeting is scheduled by the non-CDA user, then the CDA user may observe an unusual start time. However, because CDA time is designed to gently and gradually adjust the time by up to approximately one hour on either side of a transition, these time differences should never be more than approximately one hour. Any time difference that is greater than an hour will be an artifact not of CDA time itself, but rather of the differences between geographic time zones.

The foregoing can be used to build or embody several example implementations, according to the teachings of the present specification. Some example implementations are included here as non-limiting illustrations of these teachings.

There is disclosed herein an example method of observing continuous daylight adjustment (CDA) time, comprising: commencing at a first transition date observing an annual spring-forward period comprising lengthened social seconds, wherein a lengthened social second is longer than a standard scientific second; commencing at a second transition date observing an annual fall-back period comprising shortened social seconds, wherein a shortened social second is shorter than a standard scientific second; and computing and electronically displaying in a human-readable format a current social time different from a current scientific time.

There is further disclosed an example method, wherein the first transition date is an absolute Gregorian date.

There is further disclosed an example method, wherein the first transition date is a relative date.

There is further disclosed an example method, wherein the first transition date is in the range February to April in earth's northern hemisphere and August to October in earth's southern hemisphere.

There is further disclosed an example method, wherein the second transition date is in the range August to October in earth's northern hemisphere, and February to April in earth's southern hemisphere.

There is further disclosed an example method, wherein the first transition date is at or near a spring equinox, and the second transition date is at or near an autumn equinox.

There is further disclosed an example method, wherein the first transition date is at or near a summer solstice, and the second transition date is at or near a winter solstice.

There is further disclosed an example method, wherein the spring-forward period has approximately an 8:4 relation to the fall-back period.

There is further disclosed an example method, wherein the spring-forward period has approximately a 6:6 relation to the fall-back period.

There is further disclosed an example method, wherein the lengthened social second is substantially 1.00022894 scientific seconds.

There is further disclosed an example method, wherein the lengthened social seconds are selected to add between approximately 14 and 30 scientific seconds per day.

There is further disclosed an example method, wherein the shortened social second is substantially 0.99977231 scientific seconds.

There is further disclosed an example method, wherein the shortened social seconds are selected to remove between approximately 14 and 30 scientific second per day.

There is further disclosed an example method, further comprising displaying an unadjusted scientific time alongside the social time.

There is further disclosed an example apparatus comprising means for performing the method of a number of the above examples.

There is further disclosed an example apparatus, wherein the means for performing the method comprise a processor and a memory.

There is further disclosed an example apparatus, wherein the memory comprises machine-readable instructions that, when executed, cause the apparatus to perform the method of a number of the above examples.

There is further disclosed an example apparatus, wherein the apparatus is a computing system.

There is further disclosed an example of at least one computer readable medium comprising instructions that, when executed, implement a method or realize an apparatus as illustrated in a number of the above examples.

There is also disclosed an example network time protocol (NTP) server, comprising: a hardware platform comprising a processor and a memory; a network interface; a first timing circuit to keep scientific time; a second timing circuit to keep social time according to a social second that is semi-annually transitioned between social seconds that are alternately lengthened and shortened from a standard scientific second; and logic encoded within the memory to instruct the processor to: receive via the network interface an NTP time request packet; parse a header of the NTP time request packet to determine a time request type; and return via the network interface one of the social time or the scientific time depending on the time request type.

There is further disclosed an example NTP server, wherein the logic is further to instruct the processor to query a high-precision time source via the network interface for a current scientific time.

There is further disclosed an example NTP server, wherein the logic is further to instruct the processor to compute the social time from the scientific time.

There is further disclosed an example NTP server, wherein computing the social time comprises computing a number of scientific seconds since a continuous daylight adjustment (CDA) transition, and multiplying by a lengthened or shortened social second.

There is further disclosed an example NTP server, wherein the logic is responsive to a transition date, the transition date comprising an absolute Gregorian date.

There is further disclosed an example NTP server, wherein the logic is responsive to a transition date, the transition date comprising a relative date.

There is further disclosed an example NTP server, wherein the logic is responsive to a first transition date, the first transition date comprising a date in the range February to April in earth's northern hemisphere and August to October in earth's southern hemisphere.

There is further disclosed an example NTP server, wherein the logic is responsive to a second transition date, the second transition date comprising a date in the range August to October in earth's northern hemisphere, and February to April in earth's southern hemisphere.

There is further disclosed an example NTP server, wherein the logic is responsive to first and second transition dates, the first transition date comprising a date at or near a spring equinox, and the second transition date comprising a date at or near an autumn equinox.

There is further disclosed an example NTP server, wherein the logic is responsive to first and second transition dates, the first transition date comprising a date at or near a summer solstice, and the second transition date comprising a date at or near a winter solstice.

There is further disclosed an example NTP server, wherein the logic is responsive to a spring-forward period that has approximately an 8:4 relation to a fall-back period.

There is further disclosed an example NTP server, wherein the logic is responsive to a spring-forward period that has approximately a 6:6 relation to a fall-back period.

There is further disclosed an example NTP server, wherein returning the social time via the network interface comprises computing the social time based on lengthened social seconds substantially equivalent to 1.00022894 scientific seconds.

There is further disclosed an example NTP server, wherein the lengthened social seconds are selected to add between approximately 14 and 30 scientific seconds per day.

There is further disclosed an example NTP server, wherein returning the social time via the network interface comprises computing the social time based on shortened social seconds substantially equivalent to 0.99977231 scientific seconds.

There is further disclosed an example NTP server, wherein the shortened social seconds are selected to remove between approximately 14 and 30 scientific second per day.

There is further disclosed an example NTP server, further comprising an interface for displaying an unadjusted scientific time alongside the social time.

There is also disclosed a mechanical time-keeping device, comprising gears having a first gearing ratio corresponding to a lengthened social second, and a second gearing ratio corresponding to a shortened social second; and transition means to transition between the first and second gearing ratios.

There is further disclosed an example mechanical time-keeping device, wherein the transition means comprise a manual toggle.

There is further disclosed an example mechanical time-keeping device, further comprising date-keeping means.

There is further disclosed an example mechanical time-keeping device, wherein the transition means are automated.

There is further disclosed an example mechanical time-keeping device, wherein the transition means are to transition between the first and second gearing ratios based on an absolute Gregorian date.

There is further disclosed an example mechanical time-keeping device, wherein the transition means are to transition between the first and second gearing ratios based on a relative date.

There is further disclosed an example mechanical time-keeping device, wherein the transition means are to transition between the first and second gearing ratios on a first date in the range February to April in earth's northern hemisphere and August to October in earth's southern hemisphere.

There is further disclosed an example mechanical time-keeping device, wherein the transition means are to transition between the first and second gearing ratios on a second date in the range August to October in earth's northern hemisphere, and February to April in earth's southern hemisphere.

There is further disclosed an example mechanical time-keeping device, wherein the transition means are to transition between the first and second gearing ratios on dates at or near a spring equinox and an autumn equinox.

There is further disclosed an example mechanical time-keeping device, wherein the transition means are to transition between the first and second gearing ratios on dates at or near a summer solstice and a winter solstice.

There is further disclosed an example mechanical time-keeping device, wherein the transition means are to transition between the first and second gearing ratios based on a spring-forward period with approximately an 8:4 relation to the fall-back period.

There is further disclosed an example mechanical time-keeping device, wherein the transition means are to transition between the first and second gearing ratios based on a spring-forward period with approximately a 6:6 relation to the fall-back period.

There is further disclosed an example mechanical time-keeping device, wherein the lengthened social second is substantially 1.00022894 scientific seconds.

There is further disclosed an example mechanical time-keeping device, wherein the gears are machined according to lengthened social seconds selected to add between approximately 14 and 30 scientific seconds per day.

There is further disclosed an example mechanical time-keeping device, wherein the shortened social second is substantially 0.99977231 scientific seconds.

There is further disclosed an example mechanical time-keeping device, wherein the gears are machined according to shortened social seconds selected to remove between approximately 14 and 30 scientific second per day.

There is further disclosed an example mechanical time-keeping device, further comprising an interface to display an unadjusted scientific time alongside a social time.

There is further disclosed an example wall clock comprising a mechanical time-keeping device.

There is further disclosed an example grandfather clock comprising a mechanical time-keeping device.

There is further disclosed an example wrist watch comprising a mechanical time-keeping device.

There is also disclosed an example electronic computing device, comprising: a microprocessor circuit; a timing circuit; and instructions encoded within a memory to compute and display a social time different from a standard scientific time, comprising computing a number of social seconds elapsed since a transition date, wherein social seconds have a first value greater than a standard scientific second during a first annual period, and a second value less than a standard scientific second during a second annual period.

There is further disclosed an example electronic computing device, wherein the timing circuit is a crystal oscillator.

There is further disclosed an example electronic computing device, wherein the transition date is an absolute Gregorian date.

There is further disclosed an example electronic computing device, wherein the transition date is a relative date.

There is further disclosed an example electronic computing device, wherein the first annual period begins in the range February to April in earth's northern hemisphere and August to October in earth's southern hemisphere.

There is further disclosed an example electronic computing device, wherein the second annual period begins in the range August to October in earth's northern hemisphere, and February to April in earth's southern hemisphere.

There is further disclosed an example electronic computing device, wherein the first annual period begins at or near a spring equinox, and the second annual period begins at or near an autumn equinox.

There is further disclosed an example electronic computing device, wherein the first annual period begins at or near a summer solstice, and the second annual period begins at or near a winter solstice.

There is further disclosed an example electronic computing device, wherein the first annual period has approximately an 8:4 relation to the second annual period.

There is further disclosed an example electronic computing device, wherein the first annual period has approximately a 6:6 relation to the second annual period.

There is further disclosed an example electronic computing device, wherein the social seconds of the first annual period are substantially 1.00022894 scientific seconds.

There is further disclosed an example electronic computing device, wherein the social seconds of the first annual period are selected to add between approximately 14 and 30 scientific seconds per day.

There is further disclosed an example electronic computing device, wherein the social seconds of the second annual period are substantially 0.99977231 scientific seconds.

There is further disclosed an example electronic computing device, wherein the social seconds of the second annual period are selected to remove between approximately 14 and 30 scientific second per day.

There is further disclosed an example electronic computing device, further comprising an interface to display an unadjusted scientific time alongside the social time.

There is further disclosed an example electronic wristwatch, comprising the electronic computing device of a number of the above examples.

There is further disclosed an example smart phone, comprising the electronic computing device of a number of the above examples.

There is further disclosed an example tablet computer, comprising the electronic computing device of a number of the above examples.

There is further disclosed an example desktop or laptop computer, comprising the electronic computing device of a number of the above examples.

A system for providing a continuous time adjustment DST method and apparatus will now be described with more particular reference to the attached FIGURES. It should be noted that throughout the FIGURES, certain reference numerals may be repeated to indicate that a particular device or block is referenced multiple times across several FIGURES. In other cases, similar elements may be given new numbers in different FIGURES. Neither of these practices is intended to require a particular relationship between the various embodiments disclosed. In certain examples, a genus or class of elements may be referred to by a reference numeral ("widget 10"), while individual species or examples of the element may be referred to by a hyphenated numeral ("first specific widget 10-1" and "second specific widget 10-2").

FIG. 1 is a block diagram of an interconnected computing ecosystem 100. In the example of FIG. 1, computing ecosystem 100 may be provided within an enterprise, a government entity, a data center, a telecommunications provider, a "smart home" with computers, smart phones, and various internet of things (IoT) devices, or any other suitable ecosystem. Computing ecosystem 100 is provided herein as an illustrative and nonlimiting example of a system that may employ, and benefit from, the teachings of the present specification.

Computing ecosystem 100 may include one or more timekeeping enterprises 102. A single timekeeping enterprise 102 is illustrated here for simplicity, and could provide services to a business enterprise, a government entity, a family, a nonprofit organization, a church, or any other organization that may subscribe to a provider of time synchronization services via, for example, network time protocol (NTP) server 190.

Within computing ecosystem 100, one or more users 120 operate one or more client devices 110. A single user 120 and single client device 110 are illustrated here for simplicity, but a home or enterprise may have multiple users, each of which may have multiple devices, such as desktop computers, laptop computers, smart phones, tablets, hybrids, or similar.

Client devices 110 may be communicatively coupled to one another and to other network resources via local network 170. Local network 170 may be any suitable network or combination of one or more networks operating on one or more suitable networking protocols, including a local area network, a home network, an intranet, a virtual network, a wide area network, a wireless network, a cellular network, or the internet (optionally accessed via a proxy, virtual machine, or other similar security mechanism), by way of nonlimiting example. Local network 170 may also include one or more servers, firewalls, routers, switches, security appliances, or other network devices, which may be single-purpose appliances, virtual machines, containers, or functions. Some functions may be provided on client devices 110.

In this illustration, local network 170 is shown as a single network for simplicity, but in some embodiments, local network 170 may include any number of networks, such as one or more intranets connected to the internet. Local network 170 may also provide access to an external network, such as the internet, via external network 172. External network 172 may similarly be any suitable type of network.

Local network 170 may connect to the internet via gateway 108, which may be responsible, among other things, for providing a logical boundary between local network 170 and external network 172. Local network 170 may also provide services such as dynamic host configuration protocol (DHCP), gateway services, router services, and switching services, and may act as a portal across local boundary 104.

In some embodiments, gateway 108 could be a simple home router, or could be a sophisticated enterprise infrastructure including routers, gateways, firewalls, security services, deep packet inspection, web servers, or other services.

In further embodiments, gateway 108 may be a standalone internet appliance. Such embodiments are popular in cases in which computing ecosystem 100 includes a home or small business. In other cases, gateway 108 may run as a virtual machine or in another virtualized manner. In larger enterprises that feature service function chaining (SFC) or network function virtualization (NFV), gateway 108 may be include one or more service functions and/or virtualized network functions.

Local network 170 may also include a number of discrete IoT devices. For example, local network 170 may include IoT functionality to control lighting 132, thermostats or other environmental controls 134, a security system 136, and any number of other devices 140. Other devices 140 may include, as illustrative and nonlimiting examples, network attached storage (NAS), computers, printers, smart televisions, smart refrigerators, smart vacuum cleaners and other appliances, and network connected vehicles.

Local network 170 may communicate across local boundary 104 with external network 172. Local boundary 104 may represent a physical, logical, or other boundary. External network 172 may include, for example, websites, servers, network protocols, and other network-based services. NTP server 190 may provide time synchronization services to local network 170.

Local network 170 may contract with or subscribe to a provider of NTP server 190, which may provide time synchronization services, patches, products, and other services.

Figure 2:
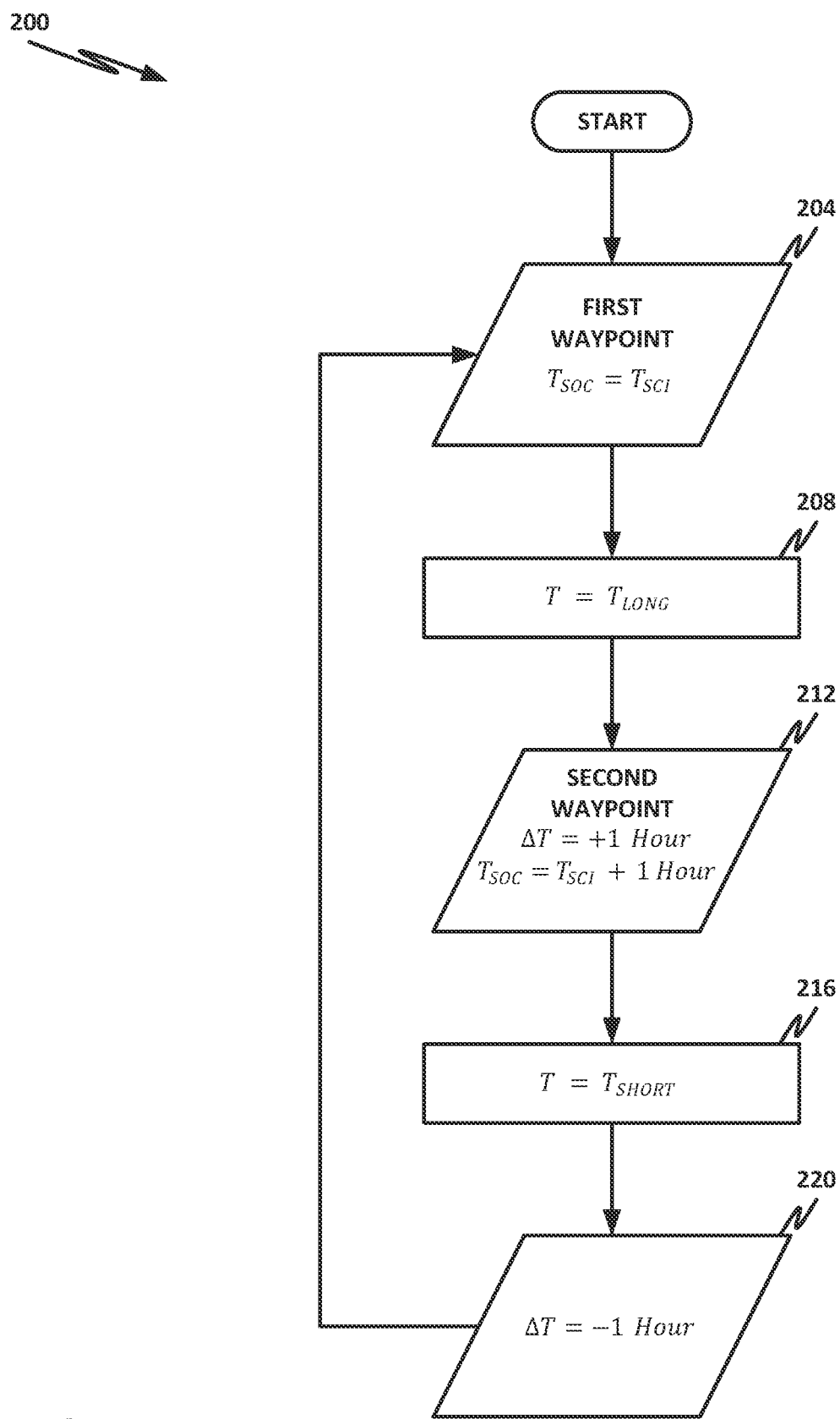
FIG. 2 is a flowchart of a method.

FIG. 2 is a flowchart of a method 200. Method 200 may be used to implement continuous daylight adjustment (CDA) systems. Method 200 could be carried out by a computing system, by a human user, or even by a whole society.

CDA system 200 starts at a first waypoint in block 204. The first waypoint could be, for example, one of the traditional times for "spring forward" or "fall back." In the current system used in the United States, daylight saving time lasts for approximately eight months, while standard time lasts for approximately four months. This same ratio could be used for CDA time, in which case the extra hour can be spread out over eight months and four months, respectively. Furthermore, CDA waypoints could be at approximately the same times. However, to make the system more deterministic, it may be desirable in some cases to use a definite date, such as November 1st to begin "fall back" time, and March 1st to begin "spring forward" time. In broad terms, the first waypoint of block 204 could be any date in January, February, March, April, May, June, July, August, September, October, November, or December. Furthermore, the waypoint could be based on a relative time, as in the current system. For example, the first waypoint could be the first Sunday of November or the last Sunday of March. However, benefits may be realized by using definite or absolute dates, because this can keep the time of a social second consistent. The use of a consistent social time is beneficial for analog clocks, which may be harder to adjust to a variable social second. Thus, it may be desirable to have each time span last for a known and definite number of days, so that the social second can be treated accordingly. For example, the 366 days of a leap year could be split into 122 days and 244 days, respectively. In another embodiment, the split could be, for example, 182 days and 184 days. In general, any time division of 365 days (or 366 days in a leap year) may be used, and in particular, a ratio between 8:4 and 6:6 may be used.

In block 208, starting at the first waypoint 204, the social second T is defined as $T_{LONG}$. This is for a spring forward span. For example, spring forward could begin on the 1st of March, at a time near the spring equinox such as March 21st, or at a time near the winter solstice such as December 22nd.

During this time span, the intent is to gain approximately one hour by expanding the length of the social second. If the winter solstice is selected as the beginning of the spring forward time, then the summer solstice may be the next transition, so that the summer solstice is not only the longest day of the year by hours of daylight, but also the day of the year on which the sun sets at the latest social time. While the teachings of this specification are consistent with any of the waypoints and divisions discussed throughout, certain embodiments will be described in connection with the use of the winter solstice and the summer solstice as waypoints, or in particular, the dates of December 22nd and June 22nd as the transitions. This is for simplicity of the discussion, and it should be understood that any other suitable dates and lengths may be substituted.

During the time of block 208, the social second is set as a long social second. In a particular example, if spring forward time commences at midnight on December 22nd and ends at midnight on June 22nd, assuming it is not a leap year, then the span is 182 days. In a leap year, the span is 183 days.

If fall back time commences at midnight on June 22nd and goes until midnight on December 22nd, the span is 183 days. Alternatively, one of the times could be adjusted by 12 hours, so that both spans are 182.5 days.

If, during the spring forward time, a social second is defined as 1.00022894 scientific seconds, then over the course of 182 days, spring forward will gain one hour (3600 seconds) within an error of less than four-hundredths of a second.

Thus, at the end of the span in block 212, the change in time will be +1 hour, within a very small margin of error. At this inflection point, a transition is made to a "fall back" social time.

Commencing at the second waypoint of block 212, the social second is defined as time $T_{SHORT}$. If the fall back time is 183 days, then if a social second of 0.99977231 scientific seconds is used, then at the end of 183 days, the time will have been adjusted by one hour (3600 seconds), within an error of less than six-hundredths of a second.

Thus, in block 220, the change in time is very close to −1 hour.

In an embodiment, to ensure that these small incremental errors in fractions of a second do not accumulate, the social time may be exactly synchronized to the scientific time (e.g., GMT, plus or minus an adjustment factor for the time zone), at midnight on the transition dates.

Advantageously, in both of these cases, a social second is extremely close to a scientific second, and the difference will be imperceptible to a human user, except in the aggregate over long spans of time, such as several months. Over several months, these differences accumulate into tens of minutes of difference, with an aggregate adjustment of approximately one hour.

Figure 3:
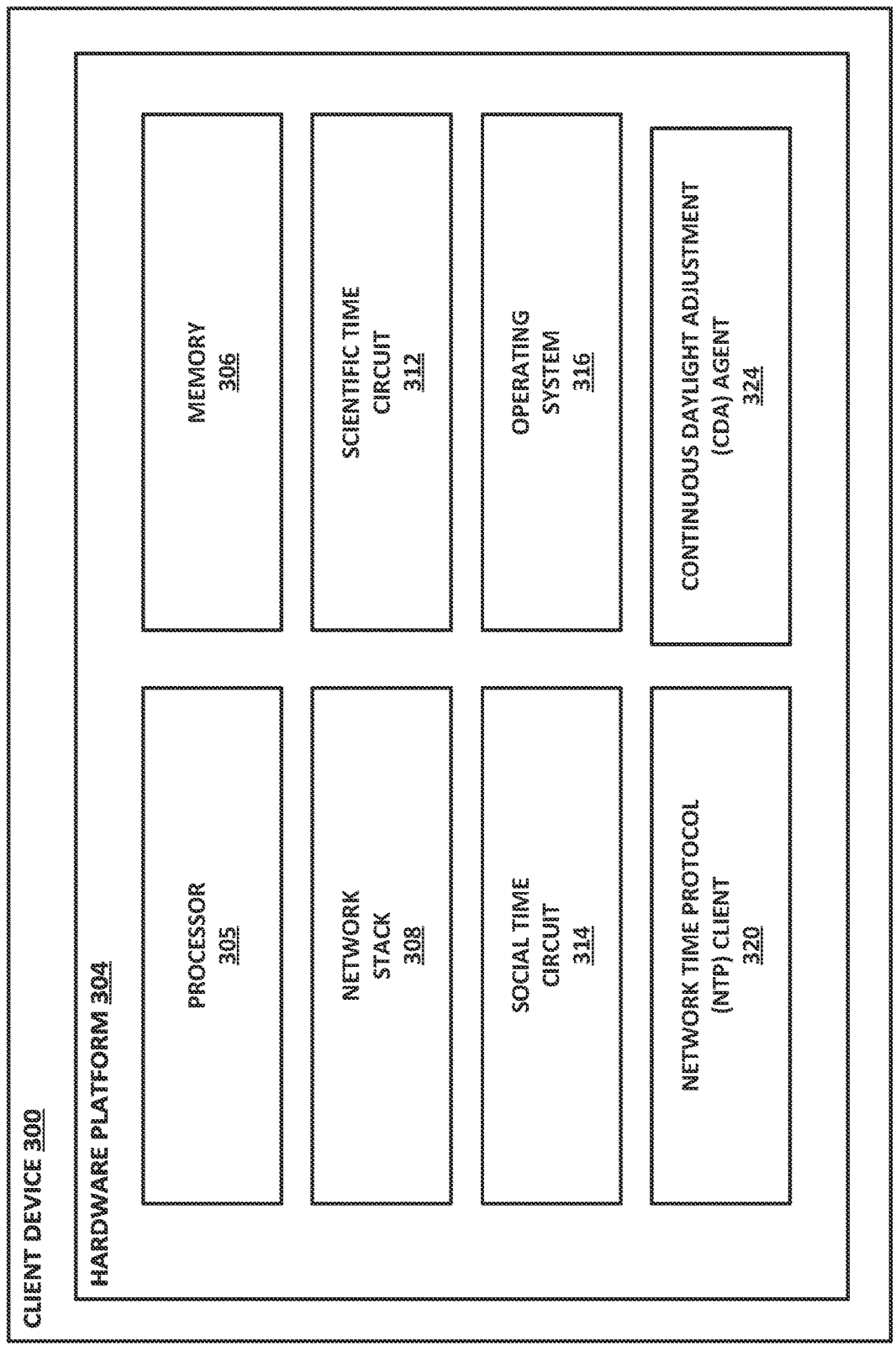
FIG. 3 is a block diagram of a client device configured for continuous daylight adjustment (CDA) time.

FIG. 3 is a block diagram of a client device 300 configured for continuous daylight adjustment (CDA) time. Client device 300 could be an endpoint device, such as a laptop or desktop computer, an enterprise server, an enterprise gateway, or some other device found within an enterprise.

Client device 300 is based on a hardware platform 304, including a processor 305 and a memory 306, which provides a physical hardware for the provision of logical functions. Examples of hardware platforms with processors and memories are disclosed in further detail in FIGS. 8-10, below. Other elements of client device 300 are provided as logical blocks, and it should be understood that these logical blocks may be hosted on hardware platform 304 as hardware, software, firmware, or a combination of these elements.

Network stack 308 may provide a traditional network stack, such as according to the transmission control protocol/internet protocol (TCP/IP) seven-layer network, or the similar open systems interconnection (OSI) seven-layer network, within data link layer 2. Client device 300 may be configured, inter alia, to operate with the network time protocol.

NTP client 320 may be configured to communicate, via network stack 308, to retrieve from an NTP server the current social and/or scientific time, as desired.

Between reconciliations with the NTP server, scientific timing circuit 312 may be configured to keep the current scientific time, while social timing circuit 314 may be configured to keep the current social time.

There are various ways in which social timing circuit 312 may operate. For example, scientific timing circuit 312 may be based on an oscillator, which oscillates with a known frequency. For keeping scientific time, these oscillations are converted via a precise formula into the value of a second, and a timestamp may be stored as the number of seconds elapsed since, for example, the Unix time epoch, which commenced on Jan. 1, 1970.

Social timing circuit 314 may use the same or a different oscillator, and different ratios may be used to calculate the social time for the current span. In one example, social time may be stored as the number of seconds elapsed since the last social time waypoint. This is particularly valuable in cases where there is some loss or gain of a fraction of a second during the spring forward or fall back time spans, in which case social time may be synchronized with GMT at the waypoints. Because the last waypoint represents a reliable exact time based on scientific time, the number of social seconds elapsed since that time is a usable measure.

CDA agent 324 may include application programming interfaces (APIs) to return both the current scientific time and the current social time. In one embodiment, an API is defined with legacy behavior and compatibility so that it does not break, for example, a portable operating system interface (POSIX) compatibility layer. In this case, the current scientific time may be returned by default. If an interface wishes to return the social time (e.g., for display to a user), then a different API call may be used to specify the return of social time.

Figure 6:
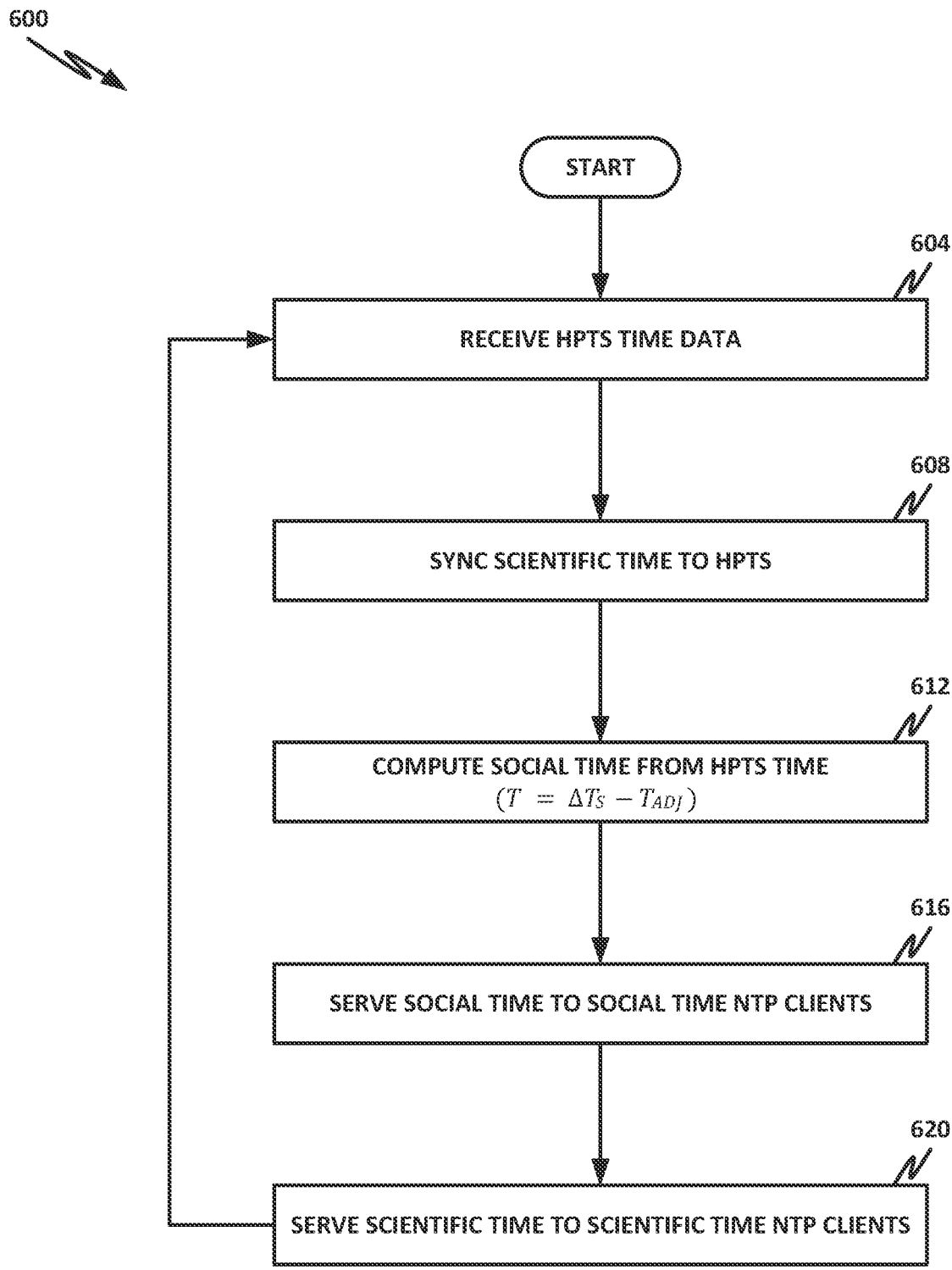
FIG. 6 is a flowchart of an additional method.

CDA agent 324 may also include, for example, a graphical user interface (GUI) such as the GUI illustrated in FIG. 6. This may allow the user to set the current social or scientific time manually, and based on that manual setting, the other (social or scientific time) may be computed. This may be useful in a case where a user does not have access to an NTP server, but still wishes to take advantage of CDA time.

Note that in some examples, a system may have only one timing circuit, and may be configured to keep track only of scientific time. This is particularly true of legacy systems. For example, a legacy operating system or computing device may not be CDA-aware. In that case, if the user wishes to use social time instead of scientific time, then the system may be configured to periodically query an NTP server that returns social time. Between queries, the system may become slightly out of sync with the current social time, such as on the order of approximately 20 seconds per day. However, if the system is configured to query an NTP server, for example, twice a day or every 12 hours, the user will never be more than approximately 10 seconds out of sync with current social time.

Figure 4:
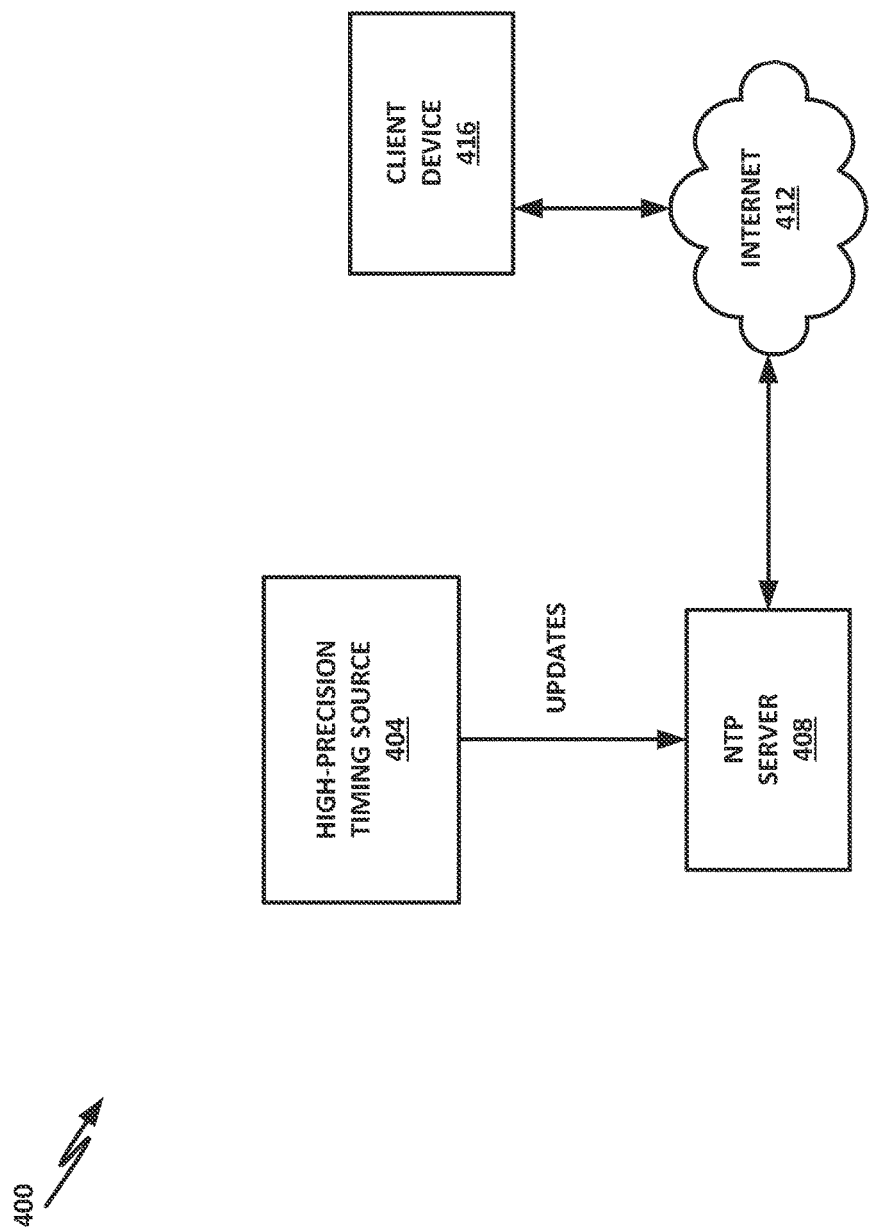
FIG. 4 is a block diagram of a timekeeping ecosystem.

FIG. 4 is a block diagram of a timekeeping ecosystem 400. Timekeeping ecosystem 400 includes a high precision timing source (HPTS) 404. HPTS 404 may be, for example, an atomic clock based on the decay of a cesium 133 atom, or other high precision timing source or equivalent. HPTS 404 may return the exact current scientific time, and may keep time with a very high precision, wherein the source loses no more than approximately a second every few thousand years.

NTP server 408 receives the current exact time from HPTS 404, and synchronizes its clock to the exact scientific time received from HPTS 404. NTP server 408 may be configured to return both the current scientific time, and the current social time under a CDA regimen.

NTP server 408 may communicate via internet 412 with one or more client devices 416. Client devices 416 may rely on NTP server 408 to provide the current time. Advantageously, client devices 416 need not have CDA-compatible circuits or systems to receive the current CDA time. Rather, NTP server 408 may be configured via at least one interface or API to return the current CDA time, and may also be configured via other interfaces or APIs to return the current scientific time. Thus, if client device 416 lacks built-in CDA capabilities, but has existing NTP synchronization capabilities, it can be configured to synchronize with NTP server 408 at regular intervals, such as once or twice a day. In a CDA regimen, if client device 416 internally keeps scientific time, it will nevertheless become out of sync with the CDA time by only a matter of tens of seconds over the course of a day. Thus, if a client device 416 synchronizes with NTP server 408 once or twice a day, it will become out of sync with the CDA time no more than 10 to 20 seconds. A variation of 10 to 20 seconds is generally considered to be within the acceptable margin of error for social time purposes.

Figure 5:
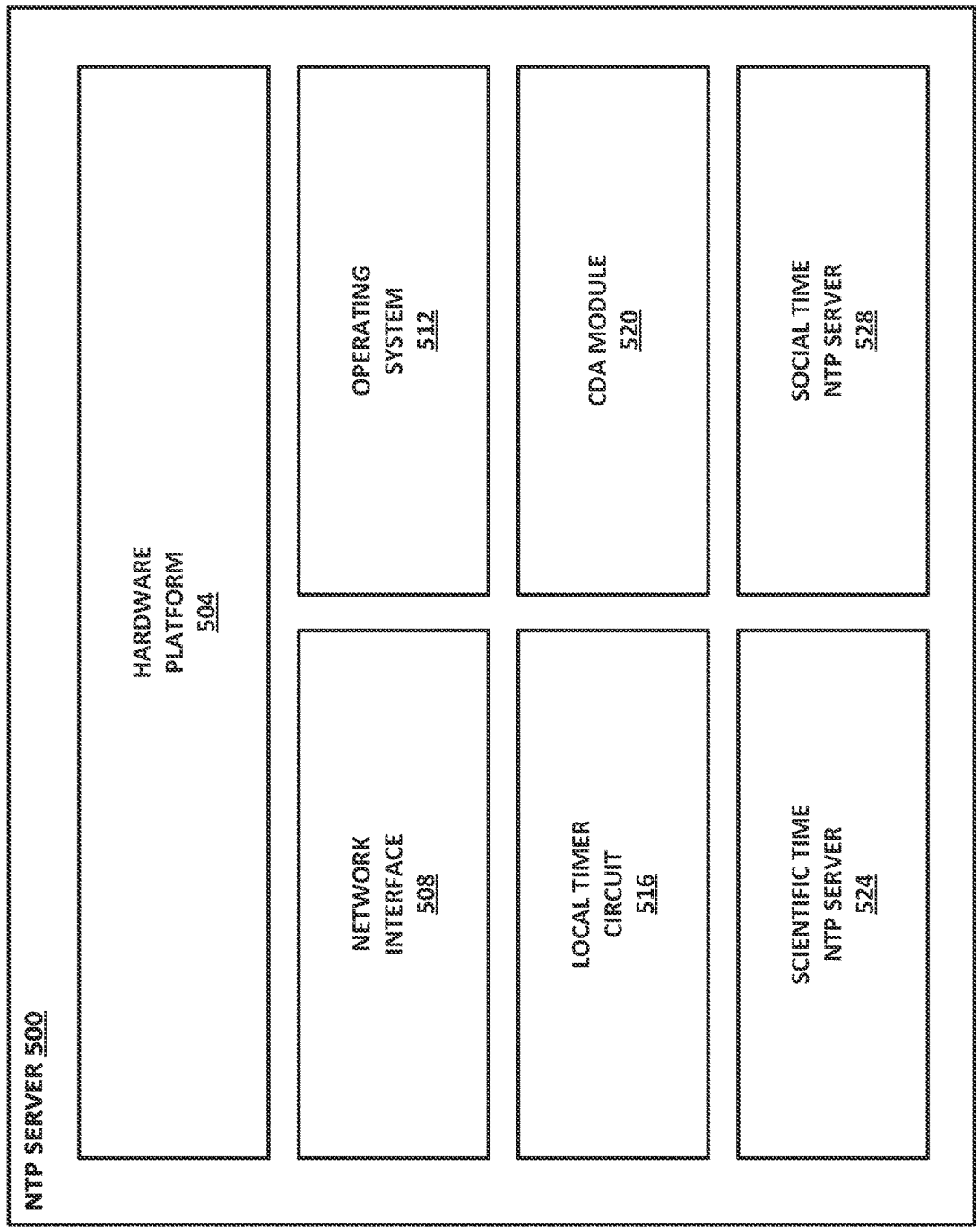
FIG. 5 is a block diagram of an NTP server.

FIG. 5 is a block diagram of an NTP server 500. NTP server 500 includes a hardware platform 504 which may include, for example, a hardware processor and/or memory, storage, and other hardware devices and interfaces.

NTP server 500 also includes a network interface 508. Network interface 508 may provide, for example, a protocol stack such as the TCP/IP or OSI seven-layer stacks, and provides communication between NTP server 500 and remote devices. Note that NTP server 500 is illustrated here as a single monolithic device, but could also be hosted on a guest infrastructure, such as in a virtual machine or on a container.

NTP server 500 includes an operating system 512. Commonly, operating system 512 may be a server-class or lightweight operating system. However, any suitable operating system may be used.

NTP server 500 includes a local timer circuit 516, which may include an oscillator or other hardware device that enables NTP server 500 to keep the current scientific and/or social time. Note that as before, there could be a single timing circuit that measures the current scientific time, or there could be dual timing circuits, such as one for scientific time and one for social time. Furthermore, there could be three timing circuits, such as one for scientific time, one for spring forward social time, and one for fall back social time.

CDA module 520 may include hardware and/or software or firmware to compute the current social or CDA time. In some examples, CDA module 520 may rely on local timer circuit 516 to provide the current scientific time, and may then compute the current social time, such as by computing the number of social seconds elapsed since the last inflection point or transition for social time.

In this example, an NTP server 500 includes a plurality of time servers. For example, scientific time server 524 may include hardware and/or software interfaces that receive a request for scientific time, and return the current scientific time. Scientific time server 524 may be configured to synchronize, for example, with an HPTS such as HPTS 404 of FIG. 4 via, for example, network interface 508. In other examples, local timer circuit 516 could itself be an HPTS, and may therefore keep highly accurate time on its own.

Social time server 528 may include hardware and/or software that keeps track of the current social time, such as by computing the number of social seconds elapsed since the last inflection point or transition. Social time NTP server 528 may be configured with interfaces and/or APIs that return the current social time, responsive to a request from a client device.

FIG. 6 is a flowchart of a method 600. Method 600 may be implemented, for example, by an NTP server such as NTP server 500, or by some other appropriate device.

Starting in block 604, the device receives HPTS time data from a high precision time source. This could be an internal time source, or it could be an external time source that is synchronized via a network or other means.

In block 608, the device syncs its current scientific time to the scientific time received from the HPTS.

In block 612, the device computes the current social time from the HPTS time. For example, the device may calculate the social time according to a difference between the scientific time and a time adjustment factor. This could include, for example, calculating the number of social seconds elapsed since an established epoch, or it could include calculating the number of social seconds elapsed since the last CDA inflection point or transition.

In block 616, responsive to requests from client devices, the server may serve the current social time to social time clients via the social time NTP server.

In block 620, responsive to requests, the system may also serve the current scientific time via the scientific NTP server to scientific NTP clients. As discussed above, differentiation between social time clients and scientific time clients could be provided via discrete interfaces, or could include the use of different headers or APIs to indicate whether social time or scientific time should be returned.

Figure 7:
FIG. 7 is a block diagram of a graphical user interface (GUI).

FIG. 7 is a block diagram of a graphical user interface (GUI) 700. GUI 700 is an illustration of a GUI that could be provided by a computing system to manage the use of both CDA and scientific time. In this example, the GUI displays both CDA and scientific time, includes an option for selecting whether to use scientific time, provides an option to select a time zone, and also provides an interface for viewing and/or changing the current date and time on the system.

In some examples, the system may be configured to keep the current scientific time according to GMT on the internal clock on the motherboard. Thus, the system clock always maintains time according to the current scientific GMT time. This means that any time the system needs to display or use social time, the system can simply use the current GMT scientific time to compute the social time, and then display the social time as necessary. In some embodiments, the computing system may be configured to perform internal operations via GMT or other scientific time bases, and use social time only for display to the user. This draws a distinction between the social time and the scientific time, and allows the user to operate socially on the social time, while allowing the computer to perform scientific or other high precision operations using the correct scientific time.

Figure 8:
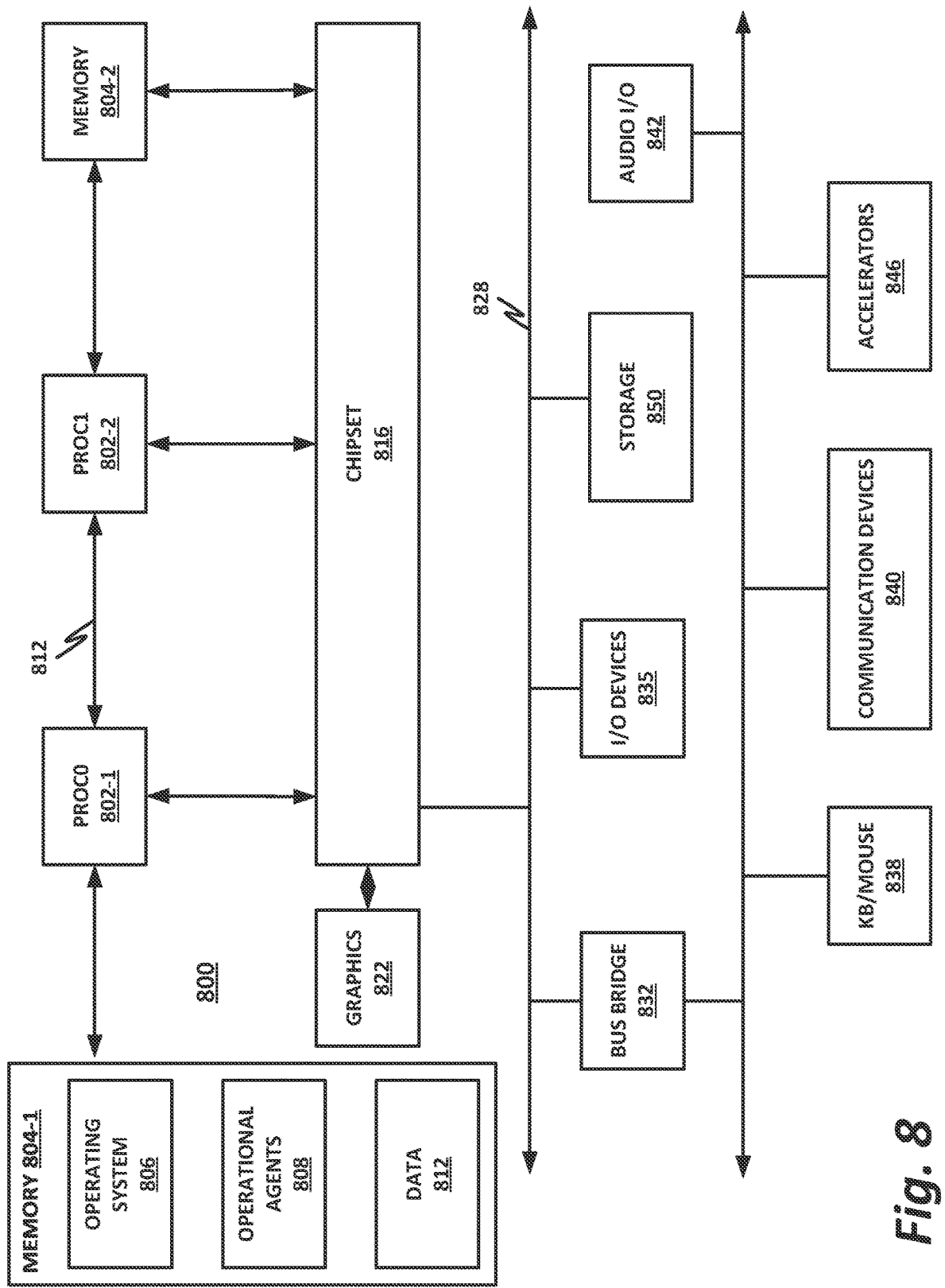
FIG. 8 is a block diagram of selected elements of a hardware platform.

FIG. 8 is a block diagram of a hardware platform 800. In at least some embodiments, hardware platform 800 may be programmed, configured, or otherwise adapted to provide the continuous time adjustment daylight saving time method according to the teachings of the present specification.

Although a particular configuration is illustrated here, there are many different configurations of hardware platforms, and this embodiment is intended to represent the class of hardware platforms that can provide a computing device. Furthermore, the designation of this embodiment as a "hardware platform" is not intended to require that all embodiments provide all elements in hardware. Some of the elements disclosed herein may be provided, in various embodiments, as hardware, software, firmware, microcode, microcode instructions, hardware instructions, hardware or software accelerators, or similar. Furthermore, in some embodiments, entire computing devices or platforms may be virtualized, on a single device, or in a data center where virtualization may span one or a plurality of devices. For example, in a "rackscale architecture" design, disaggregated computing resources may be virtualized into a single instance of a virtual device. In that case, all of the disaggregated resources that are used to build the virtual device may be considered part of hardware platform 800, even though they may be scattered across a data center, or even located in different data centers.

Hardware platform 800 is configured to provide a computing device. In various embodiments, a "computing device" may be or comprise, by way of nonlimiting example, a computer, workstation, server, mainframe, virtual machine (whether emulated or on a "bare-metal" hypervisor), network appliance, container, IoT device, high performance computing (HPC) environment, a data center, a communications service provider infrastructure (e.g., one or more portions of an Evolved Packet Core), an in-memory computing environment, a computing system of a vehicle (e.g., an automobile or airplane), an industrial control system, embedded computer, embedded controller, embedded sensor, personal digital assistant, laptop computer, cellular telephone, internet protocol (IP) telephone, smart phone, tablet computer, convertible tablet computer, computing appliance, receiver, wearable computer, handheld calculator, or any other electronic, microelectronic, or microelectromechanical device for processing and communicating data. At least some of the methods and systems disclosed in this specification may be embodied by or carried out on a computing device.

In the illustrated example, hardware platform 800 is arranged in a point-to-point (PtP) configuration. This PtP configuration is popular for personal computer (PC) and server-type devices, although it is not so limited, and any other bus type may be used.

Hardware platform 800 is an example of a platform that may be used to implement embodiments of the teachings of this specification. For example, instructions could be stored in storage 850. Instructions could also be transmitted to the hardware platform in an ethereal form, such as via a network interface, or retrieved from another source via any suitable interconnect. Once received (from any source), the instructions may be loaded into memory 804, and may then be executed by one or more processor 802 to provide elements such as an operating system 806, operational agents 808, or data 812.

Figure 10:
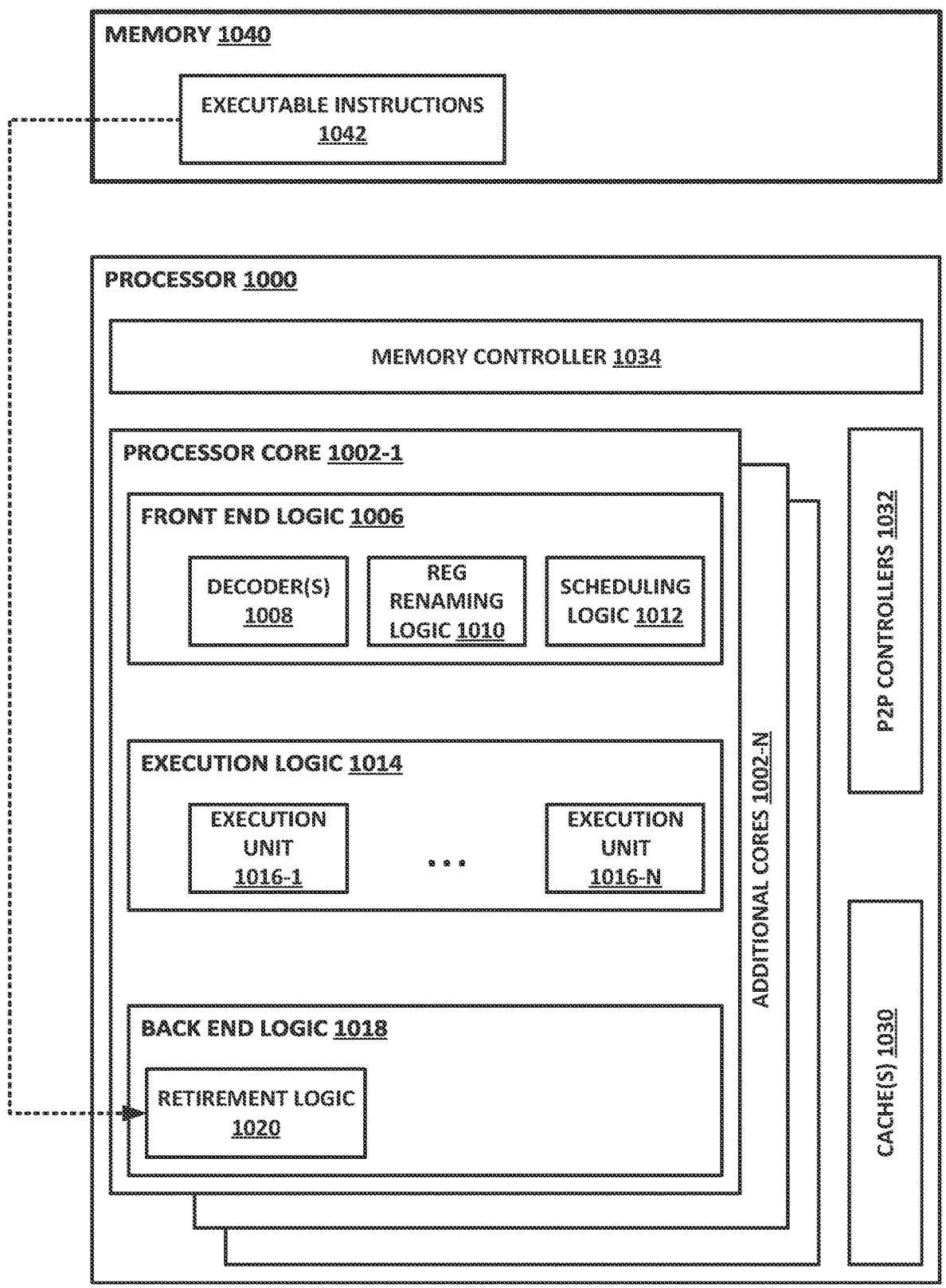
FIG. 10 is a block diagram of selected elements of a processor.

Hardware platform 800 may include several processors 802. For simplicity and clarity, only processors PROC0 802-1 and PROC1 802-2 are shown. Additional processors (such as 2, 4, 8, 16, 24, 32, 64, or 128 processors) may be provided as necessary, while in other embodiments, only one processor may be provided. Details of processors 802 are not illustrated in this FIGURE, but one embodiment is illustrated in FIG. 10. Processors may have any number of cores, such as 1, 2, 4, 8, 16, 24, 32, 64, or 128 cores.

Processors 802 may be any type of processor and may communicatively couple to chipset 816 via, for example, PtP interfaces. Chipset 816 may also exchange data with other elements, such as a high-performance graphics adapter 822. In alternative embodiments, any or all of the PtP links illustrated in FIG. 8 could be implemented as any type of bus, or other configuration rather than a PtP link. In various embodiments, chipset 816 may reside on the same die or package as a processor 802 or on one or more different dies or packages. Each chipset may support any suitable number of processors 802. A chipset 816 (which may be a chipset, uncore, Northbridge, Southbridge, or other suitable logic and circuitry) may also include one or more controllers to couple other components to one or more CPUs.

Two memories, 804-1 and 804-2 are shown, connected to PROC0 802-1 and PROC1 802-2, respectively. As an example, each processor is shown connected to its memory in a direct memory access (DMA) configuration, though other memory architectures are possible, including ones in which memory 804 communicates with a processor 802 via a bus. For example, some memories may be connected via a system bus, or in a data center, memory may be accessible in a remote DMA (RDMA) configuration.

Memory 804 may include any form of volatile or non-volatile memory including, without limitation, magnetic media (e.g., one or more tape drives), optical media, flash, random access memory (RAM), double data rate RAM (DDR RAM) non-volatile RAM (NVRAM), static RAM (SRAM), dynamic RAM (DRAM), persistent RAM (PRAM), data-centric (DC) persistent memory (e.g., Intel Optane/3D-crosspoint), cache, Layer 1 (L1) or Layer 2 (L2) memory, on-chip memory, registers, virtual memory region, read-only memory (ROM), flash memory, removable media, tape drive, cloud storage, or any other suitable local or remote memory component or components. Memory 804 may be used for short, medium, and/or long-term storage. Memory 804 may store any suitable data or information utilized by platform logic. In some embodiments, memory 804 may also comprise storage for instructions that may be executed by the cores of processors 802 or other processing elements (e.g., logic resident on chipsets 816) to provide functionality.

In certain embodiments, memory 804 may comprise a relatively low-latency volatile main memory, while storage 850 may comprise a relatively higher-latency nonvolatile memory. However, memory 804 and storage 850 need not be physically separate devices, and in some examples may represent simply a logical separation of function (if there is any separation at all). It should also be noted that although DMA is disclosed by way of nonlimiting example, DMA is not the only protocol consistent with this specification, and that other memory architectures are available.

Certain computing devices provide main memory 804 and storage 850, for example, in a single physical memory device, and in other cases, memory 804 and/or storage 850 are functionally distributed across many physical devices. In the case of virtual machines or hypervisors, all or part of a function may be provided in the form of software or firmware running over a virtualization layer to provide the logical function, and resources such as memory, storage, and accelerators may be disaggregated (i.e., located in different physical locations across a data center). In other examples, a device such as a network interface may provide only the minimum hardware interfaces necessary to perform its logical operation, and may rely on a software driver to provide additional necessary logic. Thus, each logical block disclosed herein is broadly intended to include one or more logic elements configured and operable for providing the disclosed logical operation of that block. As used throughout this specification, "logic elements" may include hardware, external hardware (digital, analog, or mixed-signal), software, reciprocating software, services, drivers, interfaces, components, modules, algorithms, sensors, components, firmware, hardware instructions, microcode, programmable logic, or objects that can coordinate to achieve a logical operation.

Graphics adapter 822 may be configured to provide a human-readable visual output, such as a command-line interface (CLI) or graphical desktop such as Microsoft Windows, Apple OSX desktop, or a Unix/Linux X Window System-based desktop. Graphics adapter 822 may provide output in any suitable format, such as a coaxial output, composite video, component video, video graphics array (VGA), or digital outputs such as digital visual interface (DVI), FPDLink, DisplayPort, or high definition multimedia interface (HDMI), by way of nonlimiting example. In some examples, graphics adapter 822 may include a hardware graphics card, which may have its own memory and its own graphics processing unit (GPU).

Chipset 816 may be in communication with a bus 828 via an interface circuit. Bus 828 may have one or more devices that communicate over it, such as a bus bridge 832, I/O devices 835, accelerators 846, communication devices 840, and a keyboard and/or mouse 838, by way of nonlimiting example. In general terms, the elements of hardware platform 800 may be coupled together in any suitable manner. For example, a bus may couple any of the components together. A bus may include any known interconnect, such as a multi-drop bus, a mesh interconnect, a fabric, a ring interconnect, a round-robin protocol, a point-to-point interconnect, a serial interconnect, a parallel bus, a coherent (e.g., cache coherent) bus, a layered protocol architecture, a differential bus, or a Gunning transceiver logic (GTL) bus, by way of illustrative and nonlimiting example.

Communication devices 840 can broadly include any communication not covered by a network interface and the various I/O devices described herein. This may include, for example, various USB, FireWire, Lightning, or other serial or parallel devices that provide communications.

I/O Devices 835 may be configured to interface with any auxiliary device that connects to hardware platform 800 but that is not necessarily a part of the core architecture of hardware platform 800. A peripheral may be operable to provide extended functionality to hardware platform 800, and may or may not be wholly dependent on hardware platform 800. In some cases, a peripheral may be a computing device in its own right. Peripherals may include input and output devices such as displays, terminals, printers, keyboards, mice, modems, data ports (e.g., serial, parallel, universal serial bus (USB), Firewire, or similar), network controllers, optical media, external storage, sensors, transducers, actuators, controllers, data acquisition buses, cameras, microphones, speakers, or external storage, by way of nonlimiting example.

In one example, audio I/O 842 may provide an interface for audible sounds, and may include in some examples a hardware sound card. Sound output may be provided in analog (such as a 3.5 mm stereo jack), component ("RCA") stereo, or in a digital audio format such as S/PDIF, AES3, AES47, HDMI, USB, Bluetooth, or Wi-Fi audio, by way of nonlimiting example. Audio input may also be provided via similar interfaces, in an analog or digital form.

Bus bridge 832 may be in communication with other devices such as a keyboard/mouse 838 (or other input devices such as a touch screen, trackball, etc.), communication devices 840 (such as modems, network interface devices, peripheral interfaces such as PCI or PCIe, or other types of communication devices that may communicate through a network), audio I/O 842, a data storage device 844, and/or accelerators 846. In alternative embodiments, any portions of the bus architectures could be implemented with one or more PtP links.

Operating system 806 may be, for example, Microsoft Windows, Linux, UNIX, Mac OS X, iOS, MS-DOS, or an embedded or real-time operating system (including embedded or real-time flavors of the foregoing). In some embodiments, a hardware platform 800 may function as a host platform for one or more guest systems that invoke application (e.g., operational agents 808).

Operational agents 808 may include one or more computing engines that may include one or more nontransitory computer-readable mediums having stored thereon executable instructions operable to instruct a processor to provide operational functions. At an appropriate time, such as upon booting hardware platform 800 or upon a command from operating system 806 or a user or security administrator, a processor 802 may retrieve a copy of the operational agent (or software portions thereof) from storage 850 and load it into memory 804. Processor 802 may then iteratively execute the instructions of operational agents 808 to provide the desired methods or functions.

As used throughout this specification, an "engine" includes any combination of one or more logic elements, of similar or dissimilar species, operable for and configured to perform one or more methods provided by the engine. In some cases, the engine may be or include a special integrated circuit designed to carry out a method or a part thereof, a field-programmable gate array (FPGA) programmed to provide a function, a special hardware or microcode instruction, other programmable logic, and/or software instructions operable to instruct a processor to perform the method. In some cases, the engine may run as a "daemon" process, background process, terminate-and-stay-resident program, a service, system extension, control panel, bootup procedure, basic in/output system (BIOS) subroutine, or any similar program that operates with or without direct user interaction. In certain embodiments, some engines may run with elevated privileges in a "driver space" associated with ring 0, 1, or 2 in a protection ring architecture. The engine may also include other hardware, software, and/or data, including configuration files, registry entries, application programming interfaces (APIs), and interactive or user-mode software by way of nonlimiting example.

Where elements of an engine are embodied in software, computer program instructions may be implemented in programming languages, such as an object code, an assembly language, or a high-level language such as OpenCL, FORTRAN, C, C++, JAVA, or HTML. These may be used with any compatible operating systems or operating environments. Hardware elements may be designed manually, or with a hardware description language such as Spice, Verilog, and VHDL. The source code may define and use various data structures and communication messages. The source code may be in a computer executable form (e.g., via an interpreter), or the source code may be converted (e.g., via a translator, assembler, or compiler) into a computer executable form, or converted to an intermediate form such as byte code. Where appropriate, any of the foregoing may be used to build or describe appropriate discrete or integrated circuits, whether sequential, combinatorial, state machines, or otherwise.

A network interface may be provided to communicatively couple hardware platform 800 to a wired or wireless network or fabric. A "network," as used throughout this specification, may include any communicative platform operable to exchange data or information within or between computing devices, including, by way of nonlimiting example, a local network, a switching fabric, an ad-hoc local network, Ethernet (e.g., as defined by the IEEE 802.3 standard), Fibre Channel, InfiniBand, Wi-Fi, or other suitable standard. Intel Omni-Path Architecture (OPA), TrueScale, Ultra Path Interconnect (UPI) (formerly called QPI or KTI), FibreChannel, Ethernet, FibreChannel over Ethernet (FCoE), InfiniBand, PCI, PCIe, fiber optics, millimeter wave guide, an internet architecture, a packet data network (PDN) offering a communications interface or exchange between any two nodes in a system, a local area network (LAN), metropolitan area network (MAN), wide area network (WAN), wireless local area network (WLAN), virtual private network (VPN), intranet, plain old telephone system (POTS), or any other appropriate architecture or system that facilitates communications in a network or telephonic environment, either with or without human interaction or intervention. A network interface may include one or more physical ports that may couple to a cable (e.g., an Ethernet cable, other cable, or waveguide).

In some cases, some or all of the components of hardware platform 800 may be virtualized, in particular the processor(s) and memory. For example, a virtualized environment may run on OS 806, or OS 806 could be replaced with a hypervisor or virtual machine manager. In this configuration, a virtual machine running on hardware platform 800 may virtualize workloads. A virtual machine in this configuration may perform essentially all of the functions of a physical hardware platform.

In a general sense, any suitably-configured processor can execute any type of instructions associated with the data to achieve the operations illustrated in this specification. Any of the processors or cores disclosed herein could transform an element or an article (for example, data) from one state or thing to another state or thing. In another example, some activities outlined herein may be implemented with fixed logic or programmable logic (for example, software and/or computer instructions executed by a processor).

Various components of the system depicted in FIG. 8 may be combined in a system-on-a-chip (SoC) architecture or in any other suitable configuration. For example, embodiments disclosed herein can be incorporated into systems including mobile devices such as smart cellular telephones, tablet computers, personal digital assistants, portable gaming devices, and similar. These mobile devices may be provided with SoC architectures in at least some embodiments. An example of such an embodiment is provided in FIG. 9. Such an SoC (and any other hardware platform disclosed herein) may include analog, digital, and/or mixed-signal, radio frequency (RF), or similar processing elements. Other embodiments may include a multichip module (MCM), with a plurality of chips located within a single electronic package and configured to interact closely with each other through the electronic package. In various other embodiments, the computing functionalities disclosed herein may be implemented in one or more silicon cores in application-specific integrated circuits (ASICs), field-programmable gate arrays (FPGAs), and other semiconductor chips.

Figure 9:
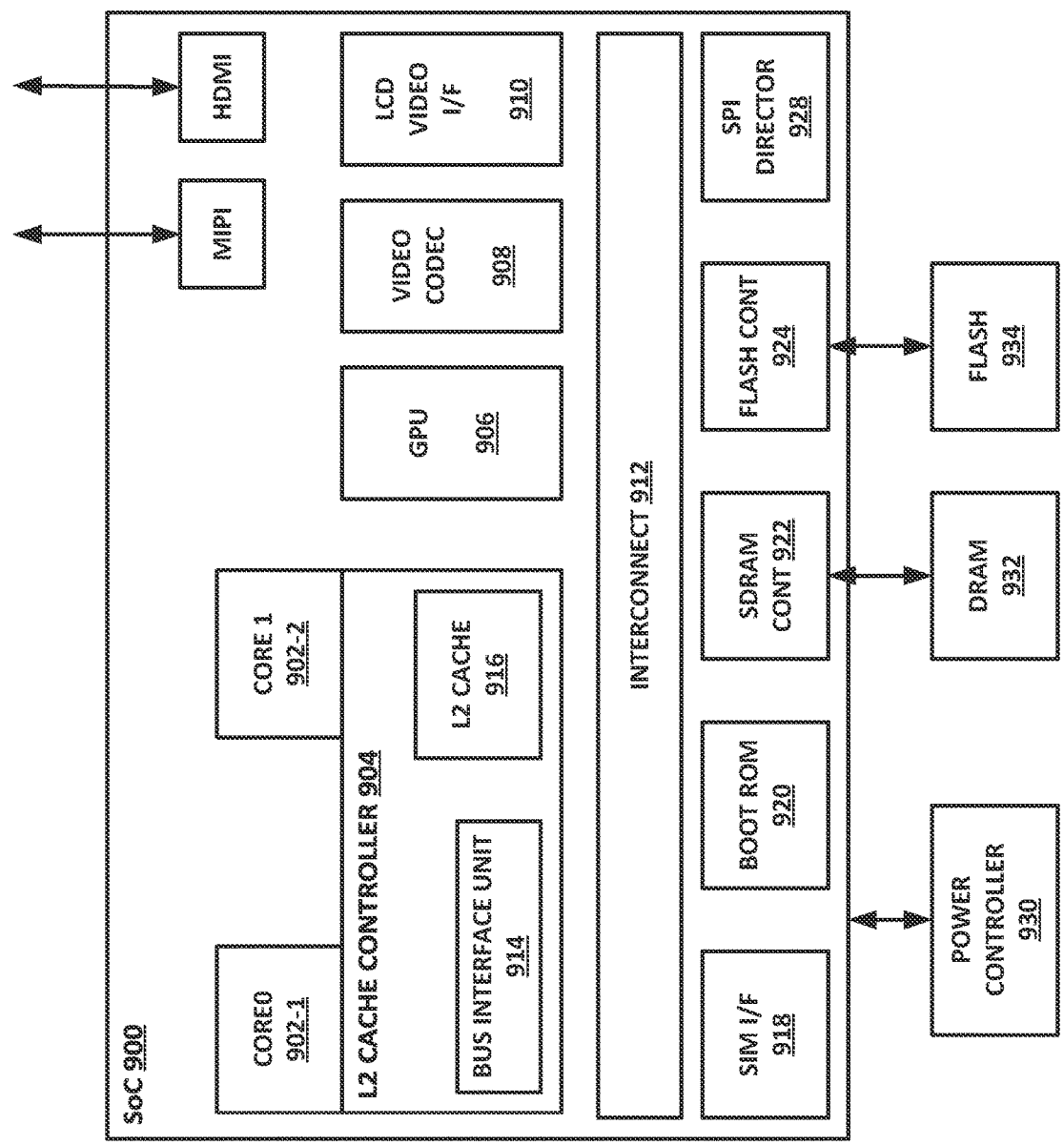
FIG. 9 is a block diagram of selected elements of a system-on-a-chip (SoC).

FIG. 9 is a block illustrating selected elements of an example SoC 900. In at least some embodiments, SoC 900 may be programmed, configured, or otherwise adapted to provide the continuous time adjustment daylight saving time method according to the teachings of the present specification.

At least some of the teachings of the present specification may be embodied on an SoC 900, or may be paired with an SoC 900. SoC 900 may include, or may be paired with, an advanced reduced instruction set computer machine (ARM) component. For example, SoC 900 may include or be paired with any ARM core, such as A-9, A-15, or similar. This architecture represents a hardware platform that may be useful in devices such as tablets and smartphones, by way of illustrative example, including Android phones or tablets, iPhone (of any version), iPad, Google Nexus, Microsoft Surface. SoC 900 could also be integrated into, for example, a personal computer, server, video processing components, laptop computer, notebook computer, netbook, or touch-enabled device.

As with hardware platform 800 above, SoC 900 may include multiple cores 902-1 and 902-2. In this illustrative example, SoC 900 also includes an L2 cache control 904, a graphics processing unit (GPU) 906, a video codec 908, a liquid crystal display (LCD) I/F 910 and an interconnect 912. L2 cache control 904 can include a bus interface unit 914, a L2 cache 916. Liquid crystal display (LCD) I/F 910 may be associated with mobile industry processor interface (MIPI)/high-definition multimedia interface (HDMI) links that couple to an LCD.

SoC 900 may also include a subscriber identity module (SIM) I/F 918, a boot read-only memory (ROM) 920, a synchronous dynamic random-access memory (SDRAM) controller 922, a flash controller 924, a serial peripheral interface (SPI) director 928, a suitable power control 930, a dynamic RAM (DRAM) 932, and flash 934. In addition, one or more embodiments include one or more communication capabilities, interfaces, and features such as instances of Bluetooth, a 3G modem, a global positioning system (GPS), and an 802.11 Wi-Fi.

Designers of integrated circuits such as SoC 900 (or other integrated circuits) may use intellectual property (IP) blocks to simplify system design. An IP block is a modular, self-contained hardware block that can be easily integrated into the design. Because the IP block is modular and self-contained, the integrated circuit (IC) designer need only "drop in" the IP block to use the functionality of the IP block. The system designer can then make the appropriate connections to inputs and outputs.

IP blocks are often "black boxes." In other words, the system integrator using the IP block may not know, and need not know, the specific implementation details of the IP block. Indeed, IP blocks may be provided as proprietary third-party units, with no insight into the design of the IP block by the system integrator.

For example, a system integrator designing an SoC for a smart phone may use IP blocks in addition to the processor core, such as a memory controller, a nonvolatile memory (NVM) controller, Wi-Fi, Bluetooth, GPS, a fourth or fifth-generation network (4G or 5G), an audio processor, a video processor, an image processor, a graphics engine, a graphics processing unit (GPU) engine, a security controller, and many other IP blocks. In many cases, each of these IP blocks has its own embedded microcontroller.

FIG. 10 is a block diagram illustrating selected elements of a processor 1000. In at least some embodiments, processor 1000 may be programmed, configured, or otherwise adapted to provide the continuous time adjustment daylight saving time method according to the teachings of the present specification.

In various examples, and throughout this specification and the appended claims, a "processor" may include any combination of logic elements operable to execute instructions, whether loaded from memory, or implemented directly in hardware, including, by way of nonlimiting example, a microprocessor, microcontroller, central processor unit (CPU), advanced RISC (reduced instruction-set computing) machine (ARM), digital signal processor (DSP), field-programmable gate array (FPGA), graphics processing unit, programmable logic array, application-specific integrated circuit (ASIC), or virtual machine processor. In certain architectures, a multi-core processor may be provided, having for example, 2, 4, 8, 12, 16, 24, 32, 64, or 128 cores. In some embodiments, one or more co-processors or accelerators (hardware or software) may also be provided for specialized or support functions. In general, processor 1000 may include any number of processing elements, which may be symmetrical or asymmetrical.

As used throughout this specification and the appended claims, a "hardware platform" identifies a genus of hardware devices, such as those commonly known as "von Neumann" machines. In general terms, a hardware platform includes at least one processor, and at least one memory. The memory may be split into volatile or main memory, and non-volatile or slower memory that is used for storage. However, this split in memory is not necessary, and in some hardware platforms, a single memory structure is used. The hardware platform genus includes a wide range of devices, spanning from single-purpose embedded computers running on an application-specific integrated circuit (ASIC), or running on a special purpose processor or DSP, and also includes devices such as smartphones, tablets, laptop computers, two-in-one computers, desktop computers, standalone servers, and various classes of enterprise or data center devices. These may include a virtualized infrastructure, wherein certain network functions are provided via network function virtualization (NFV), and wherein the "computer" may be implemented as a virtual machine or a container running on a host architecture. This also includes so-called infrastructure as a service (IaaS), wherein devices may be provided in a disaggregated architecture. In the IaaS context, the processor, memory, storage, accelerators, and peripheral devices need not even be located on the same physical device. For example, in a disaggregated architecture, a processor may be provisioned from a processor bank, memory may be provisioned from a memory bank, storage may be provisioned from a storage bank, and accelerators may be provisioned from an accelerator bank. These may be connected only in the sense that they are connected by very fast networking interfaces, and may be located on the same server rack, or even on different server racks in different locations.

At some level, these various hardware platforms ultimately map to instructions executing on a processor, or other processing circuit. On an ASIC, the instructions may be encoded into the hardware itself, whereas in a typical von Neumann machine, the instructions are loaded from a main memory. Even in a virtualized architecture, a virtualized memory location ultimately maps to a physical memory, and even in cases where multiple VMs are running on the same host hardware, the VM operating the algorithm of interest to a particular embodiment at some point takes ownership of a physical processor—even temporarily—and executes its instructions on that processor. Thus, the term hardware architecture should be understood to broadly encompass any of these embodiments. In cases where a particular species of hardware architecture is intended, that hardware architecture may be identified more specifically, such as via terms like "smart phone" or "tablet." Otherwise, it may be broadly understood that any computing apparatus of the present specification may run on any of the hardware platforms described herein.

Examples of hardware processing elements include: a thread unit, a thread slot, a thread, a process unit, a context, a context unit, a logical processor, a hardware thread, a core, and/or any other element, which is capable of holding a state for a processor, such as an execution state or architectural state. In other words, a processing element, in one embodiment, refers to any hardware capable of being independently associated with code, such as a software thread, operating system, application, or other code. A physical processor (or processor socket) typically refers to an integrated circuit, which potentially includes any number of other processing elements, such as cores or hardware threads.

A core may refer to logic located on an integrated circuit capable of maintaining an independent architectural state, wherein each independently maintained architectural state is associated with at least some dedicated execution resources. A hardware thread may refer to any logic located on an integrated circuit capable of maintaining an independent architectural state, wherein the independently maintained architectural states share access to execution resources. A physical CPU may include any suitable number of cores. In various embodiments, cores may include one or more out-of-order processor cores or one or more in-order processor cores. However, cores may be individually selected from any type of core, such as a native core, a software managed core, a core adapted to execute a native instruction set architecture (ISA), a core adapted to execute a translated ISA, a co-designed core, or other known core. In a heterogeneous core environment (i.e. asymmetric cores), some form of translation, such as binary translation, may be utilized to schedule or execute code on one or both cores.

Processor 1000 includes one or more processor cores 1002, including core 1002-1-1002-N. Cores 1002 may be, as appropriate, single-thread cores or multi-thread cores. In multithreaded cores, more than one hardware thread may be provided at a time, and the core may therefore provide more than one logical core per physical core. The cores may be configured to execute instruction code. Each processor 1000 may include at least one shared cache 1030, which may be treated logically as part of memory 1040. Memory 1040 may include executable instructions 1042, as illustrated. Caches 1030 may be filled according to known caching techniques, and may store instructions and/or data that may be used by one or more components of processor 1000.

Processor 1000 may include an integrated memory controller (MC) 1034, to communicate with memory 1040. Memory controller 1034 may include logic and circuitry to interface with memory 1040, and may also include a cache controller to handle filling and evicting instructions and data to and from cache 1030.

By way of example, each core 1002 may include front-end logic 1006, execution logic 1014, and back-end logic 1018.

In the illustrated embodiment, front-end logic 1006 includes an instruction decoder or decoders 1008, register renaming logic 1010, and scheduling logic 1012. Decoder 1008 may decode instructions received. Register renaming logic 1010 may provide register renaming, for example to facilitate pipelining. Scheduling logic 1012 may schedule instruction execution, and may provide out-of-order (OOO) execution. Front-end logic 1006 may fetch incoming instructions, perform various processing (e.g., caching, decoding, branch predicting, etc.), and pass instructions to execution logic 1014.

Execution logic 1014 includes one or more execution units 1016-1-1016-N. Execution units 1016 may include hardware instructions and microcode to carry out the provided instructions.

Backend logic 1018 includes retirement logic 1020. Core 1002 may provide for speculative execution of instructions, branch prediction, and similar. Retirement logic 1020 may be configured to determine which predicted instructions were actually needed by the program flow.

Processor 1000 may also include a PtP controller 1032, which enables connection to an uncore, chipset, Northbridge, Southbridge, or bus, by way of example.

Figure 11:
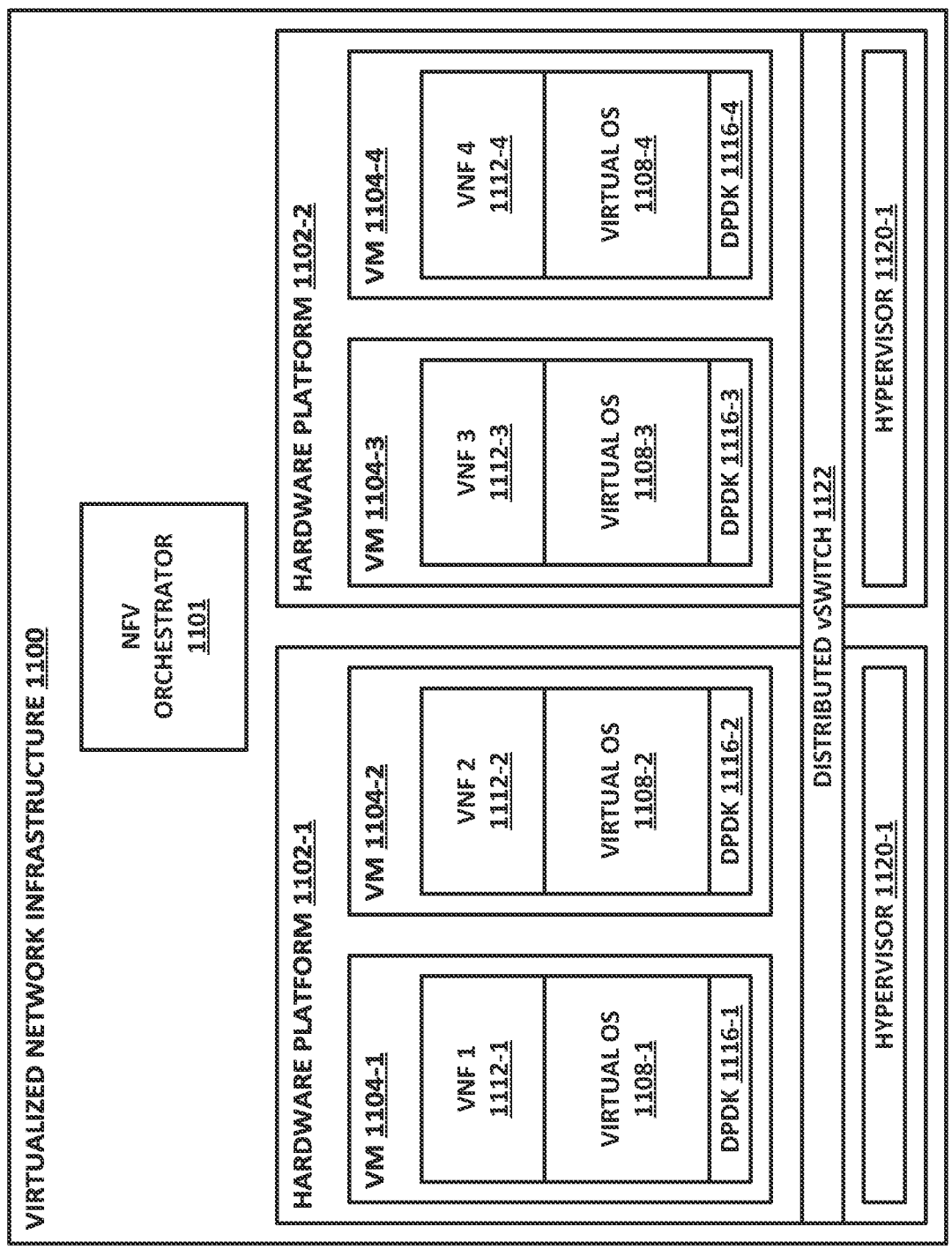
FIG. 11 is a block diagram of selected elements of a network function virtualization (NFV) infrastructure.

FIG. 11 is a block diagram of a network function virtualization (NFV) infrastructure 1100. FIG. 11 illustrates a platform for providing virtualization services. Virtualization may be used in some embodiments to provide one or more features of the present disclosure.

NFV is an aspect of network virtualization that is generally considered distinct from, but that can still interoperate with, SDN. For example, virtual network functions (VNFs) may operate within the data plane of an SDN deployment. NFV was originally envisioned as a method for providing reduced capital expenditure (Capex) and operating expenses (Opex) for telecommunication services. One feature of NFV is replacing proprietary, special-purpose hardware appliances with virtual appliances running on commercial off-the-shelf (COTS) hardware within a virtualized environment. In addition to Capex and Opex savings, NFV provides a more agile and adaptable network. As network loads change, virtual network functions (VNFs) can be provisioned ("spun up") or removed ("spun down") to meet network demands. For example, in times of high load, more load balancing VNFs may be spun up to distribute traffic to more workload servers (which may themselves be virtual machines). In times when more suspicious traffic is experienced, additional firewalls or deep packet inspection (DPI) appliances may be needed.

Because NFV started out as a telecommunications feature, many NFV instances are focused on telecommunications. However, NFV is not limited to telecommunication services. In a broad sense, NFV includes one or more VNFs running within a network function virtualization infrastructure (NFVI), such as NFVI 1100. Often, the VNFs are inline service functions that are separate from workload servers or other nodes. These VNFs can be chained together into a service chain, which may be defined by a virtual subnetwork, and which may include a serial string of network services that provide behind-the-scenes work, such as security, logging, billing, and similar.

In the example of FIG. 11, an NFV orchestrator 1101 manages a number of the VNFs 1112 running on an NFVI 1100. NFV requires nontrivial resource management, such as allocating a very large pool of compute resources among appropriate numbers of instances of each VNF, managing connections between VNFs, determining how many instances of each VNF to allocate, and managing memory, storage, and network connections. This may require complex software management, thus making NFV orchestrator 1101 a valuable system resource. Note that NFV orchestrator 1101 may provide a browser-based or graphical configuration interface, and in some embodiments may be integrated with SDN orchestration functions.

Note that NFV orchestrator 1101 itself may be virtualized (rather than a special-purpose hardware appliance). NFV orchestrator 1101 may be integrated within an existing SDN system, wherein an operations support system (OSS) manages the SDN. This may interact with cloud resource management systems (e.g., OpenStack) to provide NFV orchestration. An NFVI 1100 may include the hardware, software, and other infrastructure to enable VNFs to run. This may include a hardware platform 1102 on which one or more VMs 1104 may run. For example, hardware platform 1102-1 in this example runs VMs 1104-1 and 1104-2. Hardware platform 1102-2 runs VMs 1104-3 and 1104-4. Each hardware platform may include a hypervisor 1120, virtual machine manager (VMM), or similar function, which may include and run on a native (bare metal) operating system, which may be minimal so as to consume very few resources.

Hardware platforms 1102 may be or comprise a rack or several racks of blade or slot servers (including, e.g., processors, memory, and storage), one or more data centers, other hardware resources distributed across one or more geographic locations, hardware switches, or network interfaces. An NFVI 1100 may also include the software architecture that enables hypervisors to run and be managed by NFV orchestrator 1101.

Running on NFVI 1100 are a number of VMs 1104, each of which in this example is a VNF providing a virtual service appliance. Each VM 1104 in this example includes an instance of the Data Plane Development Kit (DPDK), a virtual operating system 1108, and an application providing the VNF 1112.

Virtualized network functions could include, as nonlimiting and illustrative examples, firewalls, intrusion detection systems, load balancers, routers, session border controllers, deep packet inspection (DPI) services, network address translation (NAT) modules, or call security association.

The illustration of FIG. 11 shows that a number of VNFs 1104 have been provisioned and exist within NFVI 1100. This FIGURE does not necessarily illustrate any relationship between the VNFs and the larger network, or the packet flows that NFVI 1100 may employ.

The illustrated DPDK instances 1116 provide a set of highly-optimized libraries for communicating across a virtual switch (vSwitch) 1122. Like VMs 1104, vSwitch 1122 is provisioned and allocated by a hypervisor 1120. The hypervisor uses a network interface to connect the hardware platform to the data center fabric (e.g., an HFI). This HFI may be shared by all VMs 1104 running on a hardware platform 1102. Thus, a vSwitch may be allocated to switch traffic between VMs 1104. The vSwitch may be a pure software vSwitch (e.g., a shared memory vSwitch), which may be optimized so that data are not moved between memory locations, but rather, the data may stay in one place, and pointers may be passed between VMs 1104 to simulate data moving between ingress and egress ports of the vSwitch. The vSwitch may also include a hardware driver (e.g., a hardware network interface IP block that switches traffic, but that connects to virtual ports rather than physical ports). In this illustration, a distributed vSwitch 1122 is illustrated, wherein vSwitch 1122 is shared between two or more physical hardware platforms 1102.

Figure 12:
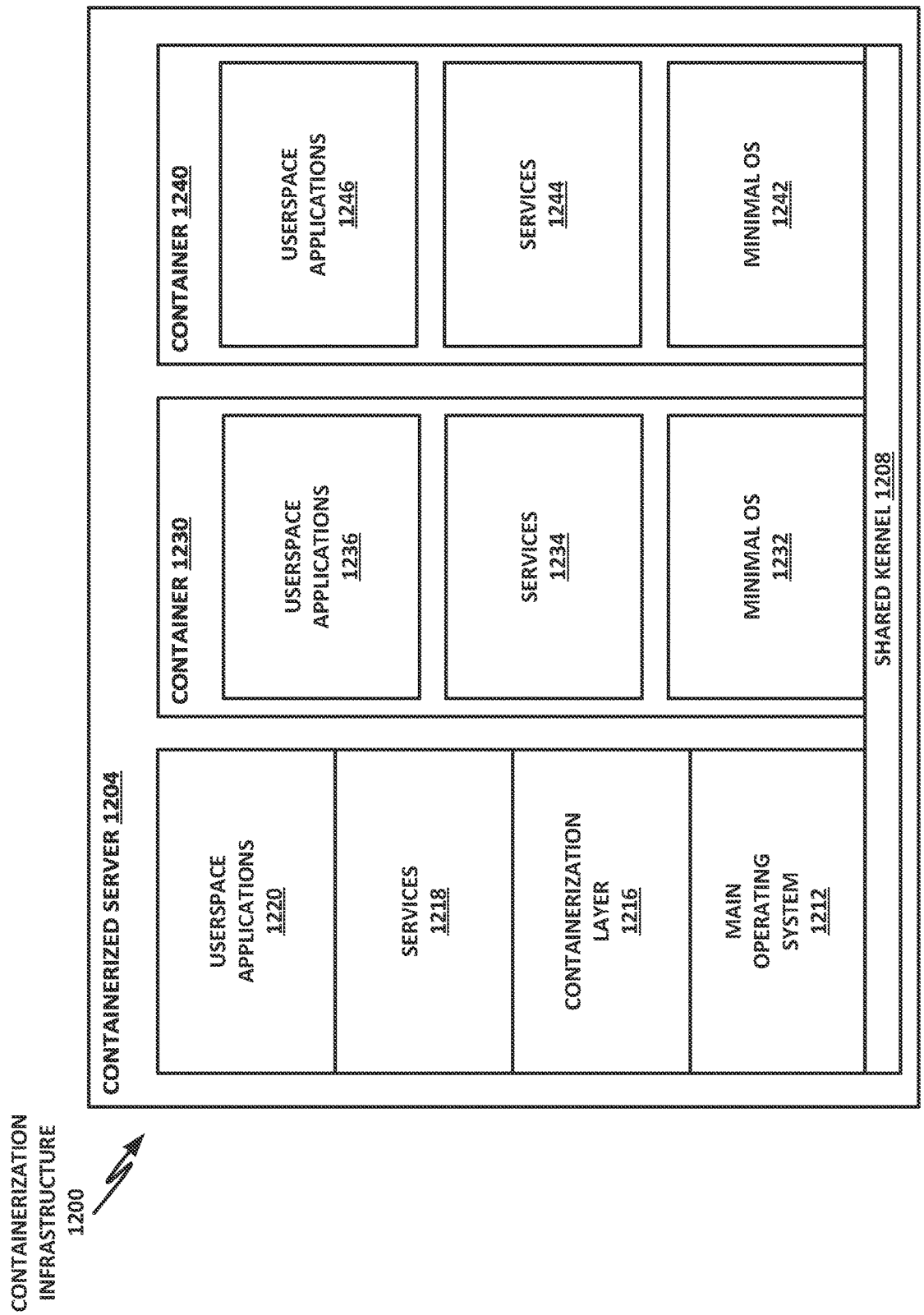
FIG. 12 is a block diagram of selected elements of a containerization infrastructure.

FIG. 12 is a block diagram of selected elements of a containerization infrastructure 1200. FIG. 12 illustrates a platform for providing containerization services. Containerization may be used in some embodiments to provide one or more features of the present disclosure. Like virtualization, containerization is a popular form of providing a guest infrastructure.

Containerization infrastructure 1200 runs on a hardware platform such as containerized server 1204. Containerized server 1204 may provide a number of processors, memory, one or more network interfaces, accelerators, and/or other hardware resources.

Running on containerized server 1204 is a shared kernel 1208. One distinction between containerization and virtualization is that containers run on a common kernel with the main operating system and with each other. In contrast, in virtualization, the processor and other hardware resources are abstracted or virtualized, and each virtual machine provides its own kernel on the virtualized hardware.

Running on shared kernel 1208 is main operating system 1212. Commonly, main operating system 1212 is a Unix or Linux-based operating system, although containerization infrastructure is also available for other types of systems, including Microsoft Windows systems and Macintosh systems. Running on top of main operating system 1212 is a containerization layer 1216. For example, Docker is a popular containerization layer that runs on a number of operating systems, and relies on the Docker daemon. Newer operating systems (including Fedora Linux 32 and later) that use version 2 of the kernel control groups service (cgroups v2) feature appear to be incompatible with the Docker daemon. Thus, these systems may run with an alternative known as Podman that provides a containerization layer without a daemon.

Various factions debate the advantages and/or disadvantages of using a daemon-based containerization layer versus one without a daemon, like Podman. Such debates are outside the scope of the present specification, and when the present specification speaks of containerization, it is intended to include containerization layers, whether or not they require the use of a daemon.

Main operating system 1212 may also include a number of services 1218, which provide services and interprocess communication to userspace applications 1220.

Services 1218 and userspace applications 1220 in this illustration are independent of any container.

As discussed above, a difference between containerization and virtualization is that containerization relies on a shared kernel. However, to maintain virtualization-like segregation, containers do not share interprocess communications, services, or many other resources. Some sharing of resources between containers can be approximated by permitting containers to map their internal file systems to a common mount point on the external file system. Because containers have a shared kernel with the main operating system 1212, they inherit the same file and resource access permissions as those provided by shared kernel 1208. For example, one popular application for containers is to run a plurality of web servers on the same physical hardware. The Docker daemon provides a shared socket, docker.sock, that is accessible by containers running under the same Docker daemon. Thus, one container can be configured to provide only a reverse proxy for mapping hypertext transfer protocol (HTTP) and hypertext transfer protocol secure (HTTPS) requests to various containers. This reverse proxy container can listen on docker.sock for newly spun-up containers. When a container spins up that meets certain criteria, such as by specifying a listening port and/or virtual host, the reverse proxy can map HTTP or HTTPS requests to the specified virtual host to the designated virtual port. Thus, only the reverse proxy host may listen on ports 80 and 443, and any request to subdomain1.example.com may be directed to a virtual port on a first container, while requests to subdomain2.example.com may be directed to a virtual port on a second container.

Other than this limited sharing of files or resources, which generally is explicitly configured by an administrator of containerized server 1204, the containers themselves are completely isolated from one another. However, because they share the same kernel, it is relatively easier to dynamically allocate compute resources such as CPU time and memory to the various containers. Furthermore, it is common practice to provide only a minimum set of services on a specific container, and the container does not need to include a full bootstrap loader because it shares the kernel with a containerization host (i.e. containerized server 1204).

Thus, "spinning up" a container is often relatively faster than spinning up a new virtual machine that provides a similar service. Furthermore, a containerization host does not need to virtualize hardware resources, so containers access those resources natively and directly. While this provides some theoretical advantages over virtualization, modern hypervisors—especially type 1, or "bare metal," hypervisors—provide such near-native performance that this advantage may not always be realized.

In this example, containerized server 1204 hosts two containers, namely container 1230 and container 1240.

Container 1230 may include a minimal operating system 1232 that runs on top of shared kernel 1208. Note that a minimal operating system is provided as an illustrative example, and is not mandatory. In fact, container 1230 may perform as full an operating system as is necessary or desirable. Minimal operating system 1232 is used here as an example simply to illustrate that in common practice, the minimal operating system necessary to support the function of the container (which in common practice, is a single or monolithic function) is provided.

On top of minimal operating system 1232, container 1230 may provide one or more services 1234. Finally, on top of services 1234, container 1230 may also provide a number of userspace applications 1236, as necessary.

Container 1240 may include a minimal operating system 1242 that runs on top of shared kernel 1208. Note that a minimal operating system is provided as an illustrative example, and is not mandatory. In fact, container 1240 may perform as full an operating system as is necessary or desirable. Minimal operating system 1242 is used here as an example simply to illustrate that in common practice, the minimal operating system necessary to support the function of the container (which in common practice, is a single or monolithic function) is provided.

On top of minimal operating system 1242, container 1240 may provide one or more services 1244. Finally, on top of services 1244, container 1240 may also provide a number of userspace applications 1246, as necessary.

Using containerization layer 1216, containerized server 1204 may run a number of discrete containers, each one providing the minimal operating system and/or services necessary to provide a particular function. For example, containerized server 1204 could include a mail server, a web server, a secure shell server, a file server, a weblog, cron services, a database server, and many other types of services. In theory, these could all be provided in a single container, but security and modularity advantages are realized by providing each of these discrete functions in a discrete container with its own minimal operating system necessary to provide those services.

The foregoing outlines features of several embodiments so that those skilled in the art may better understand various aspects of the present disclosure. The embodiments disclosed can readily be used as the basis for designing or modifying other processes and structures to carry out the teachings of the present specification. Any equivalent constructions to those disclosed do not depart from the spirit and scope of the present disclosure. Design considerations may result in substitute arrangements, design choices, device possibilities, hardware configurations, software implementations, and equipment options.

In certain embodiments, some of the components illustrated herein may be omitted or consolidated. In a general sense, the arrangements depicted in the FIGURES may be more logical in their representations, whereas a physical architecture may include various permutations, combinations, and/or hybrids of these elements.

With the numerous examples provided herein, interaction may be described in terms of two, three, four, or more electrical components. These descriptions are provided for purposes of clarity and example only. Any of the illustrated components, modules, and elements of the FIGURES may be combined in various configurations, all of which fall within the scope of this specification.

In certain cases, it may be easier to describe one or more functionalities by disclosing only selected element. Such elements are selected to illustrate specific information to facilitate the description. The inclusion of an element in the FIGURES is not intended to imply that the element must appear in the invention, as claimed, and the exclusion of certain elements from the FIGURES is not intended to imply that the element is to be excluded from the invention as claimed. Similarly, any methods or flows illustrated herein are provided by way of illustration only. Inclusion or exclusion of operations in such methods or flows should be understood the same as inclusion or exclusion of other elements as described in this paragraph. Where operations are illustrated in a particular order, the order is a nonlimiting example only. Unless expressly specified, the order of operations may be altered to suit a particular embodiment.

Other changes, substitutions, variations, alterations, and modifications will be apparent to those skilled in the art. All such changes, substitutions, variations, alterations, and modifications fall within the scope of this specification.

In order to aid the United States Patent and Trademark Office (USPTO) and, any readers of any patent or publication flowing from this specification, the Applicant: (a) does not intend any of the appended claims to invoke paragraph (f) of 35 U.S.C. section 112, or its equivalent, as it exists on the date of the filing hereof unless the words "means for" or "steps for" are specifically used in the particular claims; and (b) does not intend, by any statement in the specification, to limit this disclosure in any way that is not otherwise expressly reflected in the appended claims, as originally presented or as amended.

What is claimed is:

1. A method of observing continuous daylight adjustment (CDA) time, comprising:
    commencing, at a first transition date, to observe an annual spring-forward period, comprising observing lengthened social seconds throughout the spring-forward period, wherein a lengthened social second is longer than a standard scientific second;
    commencing, at a second transition date, to observe an annual fall-back period, comprising observing shortened social seconds throughout the fall-back period, wherein a shortened social second is shorter than a standard scientific second, and wherein the spring-forward period and the fall-back period together occupy a full calendar year; and
    computing and electronically displaying in a human-readable format a current social time different from a current scientific time.

2. The method of claim 1, wherein the first transition date is an absolute Gregorian date.

3. The method of claim 1, wherein the first transition date is a relative date.

4. The method of claim 1, wherein the first transition date is between February to April in earth's northern hemisphere and August to October in earth's southern hemisphere.

5. The method of claim 1, wherein the second transition date is between August to October in earth's northern hemisphere, and February to April in earth's southern hemisphere.

6. The method of claim 1, wherein the first transition date is at or near a spring equinox, and the second transition date is at or near an autumn equinox.

7. The method of claim 1, wherein the first transition date is at or near a summer solstice, and the second transition date is at or near a winter solstice.

8. The method of claim 1, wherein the annual spring-forward period has approximately an 8:4 relation to the annual fall-back period.

9. The method of claim 1, wherein the annual spring-forward period has approximately a 6:6 relation to the annual fall-back period.

10. The method of claim 1, wherein the lengthened social second is substantially 1.00022894 scientific seconds.

11. The method of claim 1, wherein the lengthened social seconds are selected to add between approximately 14 and 30 scientific seconds per day.

12. The method of claim 1, wherein the shortened social second is substantially 0.99977231 scientific seconds.

13. The method of claim 1, wherein the shortened social seconds are selected to remove between approximately 14 and 30 scientific second per day.

14. The method of claim 1, further comprising displaying an unadjusted scientific time alongside the current social time.

15. A network time protocol (NTP) server, comprising:
a hardware platform comprising a processor circuit and a memory;
a network interface;
a timer circuit; and
logic encoded within the memory to instruct the processor circuit to:
based on the timer circuit, compute both a social time and a scientific time, wherein the social time is computed by observing an annual spring-forward period having lengthened social seconds throughout the spring-forward period, wherein a lengthened social second is longer than a scientific second,
and by observing a fall-back period having shortened social seconds throughout the fall-back period, wherein a shortened social second is shorter than a scientific second, wherein the fall-back period and spring-forward period together occupy a full calendar year;
receive via the network interface an NTP time request packet;
parse a header of the NTP time request packet to determine a time request type;
and return via the network interface one of the social time or the scientific time depending on the time request type.

16. The NTP server of claim 15, wherein the logic is further to instruct the processor to query a high-precision time source via the network interface for a current scientific time.

17. The NTP server of claim 16, wherein the logic is further to instruct the processor to compute the social time from the scientific time.

18. The NTP server of claim 17, wherein computing the social time comprises computing a number of scientific seconds since a continuous daylight adjustment (CDA) transition, and multiplying by a lengthened or shortened social second.

19. The NTP server of claim 15, wherein the spring-forward and fall-back periods commence on respective absolute Gregorian dates.

20. The NTP server of claim 15, wherein the spring-forward and fall-back periods commence on relative dates.

21. The NTP server of claim 15, wherein the spring-forward period commences between February and April in earth's northern hemisphere and August to October in earth's southern hemisphere.

22. The NTP server of claim 15, wherein the fall-back period commences between August and October in earth's northern hemisphere, and February to April in earth's southern hemisphere.

23. The NTP server of claim 15, wherein the spring-forward period commences at or near a spring equinox, and the fall-back period commences at or near an autumn equinox.

24. The NTP server of claim 15, wherein spring-forward period commences at or near a summer solstice, and the fall-back period commences at or near a winter solstice.

25. An electronic computing device, comprising:
a microprocessor circuit;
a timing circuit; and
instructions encoded within a memory to compute and display a social time different from a standard scientific time, comprising computing a number of social seconds elapsed since a transition date, wherein social seconds have a first value greater than a standard scientific second during a first annual period, and a second value less than a standard scientific second during a second annual period, wherein the first annual period and second annual period together constitute a calendar year.

26. The electronic computing device of claim 25, wherein the timing circuit is a crystal oscillator.

27. The electronic computing device of claim 25, wherein the social seconds of the first annual period are substantially 1.00022894 scientific seconds.

28. The electronic computing device of claim 25, wherein the social seconds of the first annual period are selected to add between approximately 14 and 30 scientific seconds per day.

29. The electronic computing device of claim 25, wherein the social seconds of the second annual period are substantially 0.99977231 scientific seconds.

30. The electronic computing device of claim 25, wherein the social seconds of the second annual period are selected to remove between approximately 14 and 30 scientific second per day.

31. An electronic wristwatch, comprising the electronic computing device of claim 25.

32. An Internet of Things (IoT) device comprising the electronic computing device of claim 25.

33. An electronic clock comprising the electronic computing device of claim 25.

\* \* \* \* \*